(12) United States Patent
Ueda et al.

(10) Patent No.: US 7,981,059 B2
(45) Date of Patent: Jul. 19, 2011

(54) DRIVING FORCE CALCULATING DEVICE, DRIVING FORCE CALCULATING METHOD, POWER ASSISTING DEVICE, PROGRAM, AND COMPUTER-READABLE STORAGE MEDIUM

(75) Inventors: Jun Ueda, Ikoma (JP); Tsukasa Ogasawara, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 671 days.

(21) Appl. No.: 11/885,072

(22) PCT Filed: Aug. 4, 2005

(86) PCT No.: PCT/JP2005/014346
§ 371 (c)(1),
(2), (4) Date: Jun. 2, 2008

(87) PCT Pub. No.: WO2006/092872
PCT Pub. Date: Sep. 8, 2006

(65) Prior Publication Data
US 2009/0024061 A1 Jan. 22, 2009

(30) Foreign Application Priority Data
Feb. 28, 2005 (JP) ................................. 2005-054961

(51) Int. Cl.
*A61B 5/103* (2006.01)
*A61B 5/117* (2006.01)
(52) U.S. Cl. .......................... 600/595; 600/587; 600/594
(58) Field of Classification Search .................. 600/587, 600/594, 595; 702/127, 141–154; 901/1–50
See application file for complete search history.

(56) References Cited

U.S. PATENT DOCUMENTS
7,217,247 B2 * 5/2007 Dariush et al. .................... 601/5
(Continued)

FOREIGN PATENT DOCUMENTS
| JP | 7-313495 | 12/1995 |
| JP | 11-309184 | 11/1999 |
| JP | 2000-51289 | 2/2000 |
| JP | 2003-220102 | 8/2003 |
| JP | 2004-105261 | 4/2004 |

OTHER PUBLICATIONS

Muscle Force Design Method During Exercise Using Muscle/Artificial Muscle-Integrated Human Model(The Institute of Electronics, Information and Communication Engineers Technical Report, ISSN0913-5685, Technical Report of IEICE, vol. 104, No. 348, p. 19-24).

(Continued)

*Primary Examiner* — Jeffrey G Hoekstra
(74) *Attorney, Agent, or Firm* — Harness, Dickey & Pierce, P.L.C.

(57) ABSTRACT

In one embodiment of the present invention, a driving force calculating device calculates a driving force so that a desired load is applied on a muscle while a power assisting device assists and/or resists a predetermined motion. A driving force calculating section of a driving force calculating device calculates a driving force of each driving section according to a joint torque table on joint torque necessary for a rotational motion and an assigned muscle force table on an assigned muscle force input to a muscle force input section. For the calculation is used a muscle/artificial muscle integrated model data integrally including musculoskeletal model data on a musculoskeletal model of a human and artificial muscle model data on an artificial muscle model of the power assisting device. The driving force is calculated through optimization using Crowninshield performance function under constraint conditions of the joint torque and the assigned muscle force.

9 Claims, 15 Drawing Sheets

U.S. PATENT DOCUMENTS

| | | | |
|---|---|---|---|
| 7,402,142 B2 * | 7/2008 | Kawai et al. | 600/587 |
| 7,529,632 B2 * | 5/2009 | Ueda et al. | 702/44 |
| 7,591,166 B2 * | 9/2009 | Ueda et al. | 73/9 |
| 7,644,628 B2 * | 1/2010 | Harish | 73/780 |
| 7,693,572 B2 * | 4/2010 | Kuramori et al. | 600/546 |
| 7,713,217 B2 * | 5/2010 | Ikeuchi et al. | 600/595 |
| 2004/0116836 A1 * | 6/2004 | Kawai et al. | 600/595 |
| 2004/0158175 A1 * | 8/2004 | Ikeuchi et al. | 601/5 |
| 2008/0161937 A1 * | 7/2008 | Sankai | 623/25 |
| 2008/0202202 A1 * | 8/2008 | Ueda et al. | 73/9 |
| 2008/0216592 A1 * | 9/2008 | Ueda et al. | 73/865.4 |
| 2009/0024061 A1 * | 1/2009 | Ueda et al. | 600/595 |
| 2009/0115292 A1 * | 5/2009 | Ueda et al. | 310/338 |

OTHER PUBLICATIONS

A Three-Dimensional Kinematic Model of the Human Long Finger and the Muscles That Actuate It, J.Biggs et al., Medical Engineering & Physics, 21(19).pp. 625-639, 1999.

Inertia and Muscle Contraction Parameters For Musculoskeletal Modelling of the Shoulder Mechanism; H.E.J. Veeger et al., J. Biomechanics, vol. 24, No. 7, pp. 615-629, 1991.

Arbitary Load Force Design in Human Exercise by Power Assist System (The 22$^{nd}$ Annual Conference of The Robotics Society of Japan, Summary of lecture meeting 3K15), Sep. 15, 2004.

* cited by examiner

F I G. 1 0
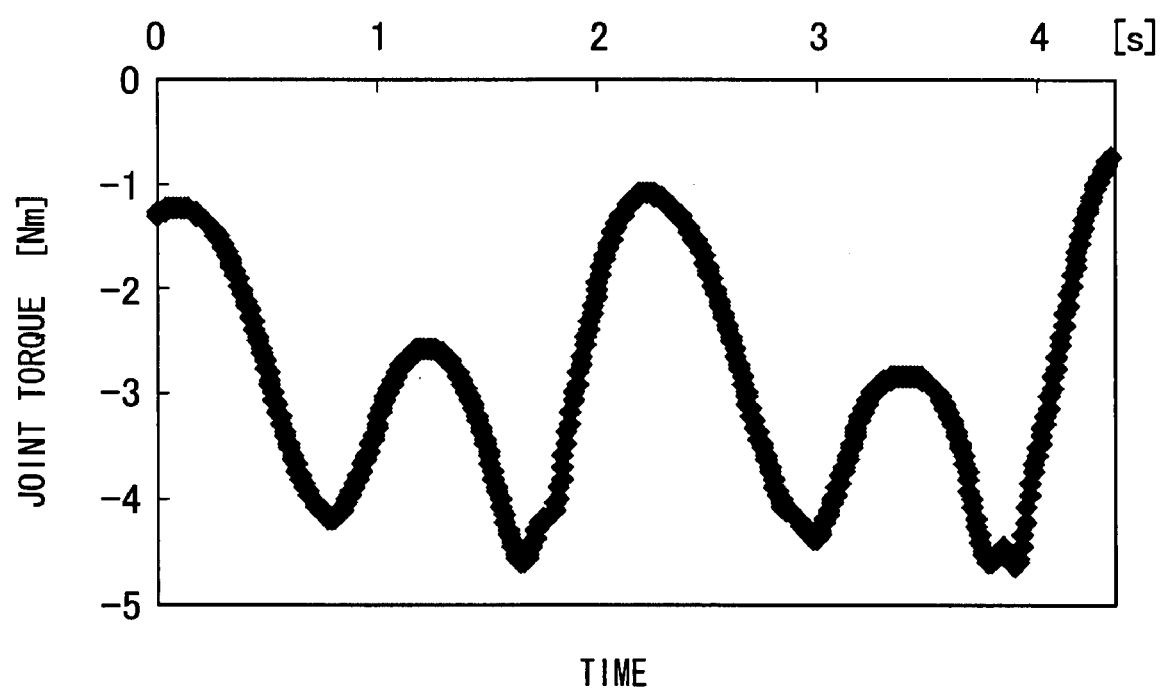

F I G. 1 3
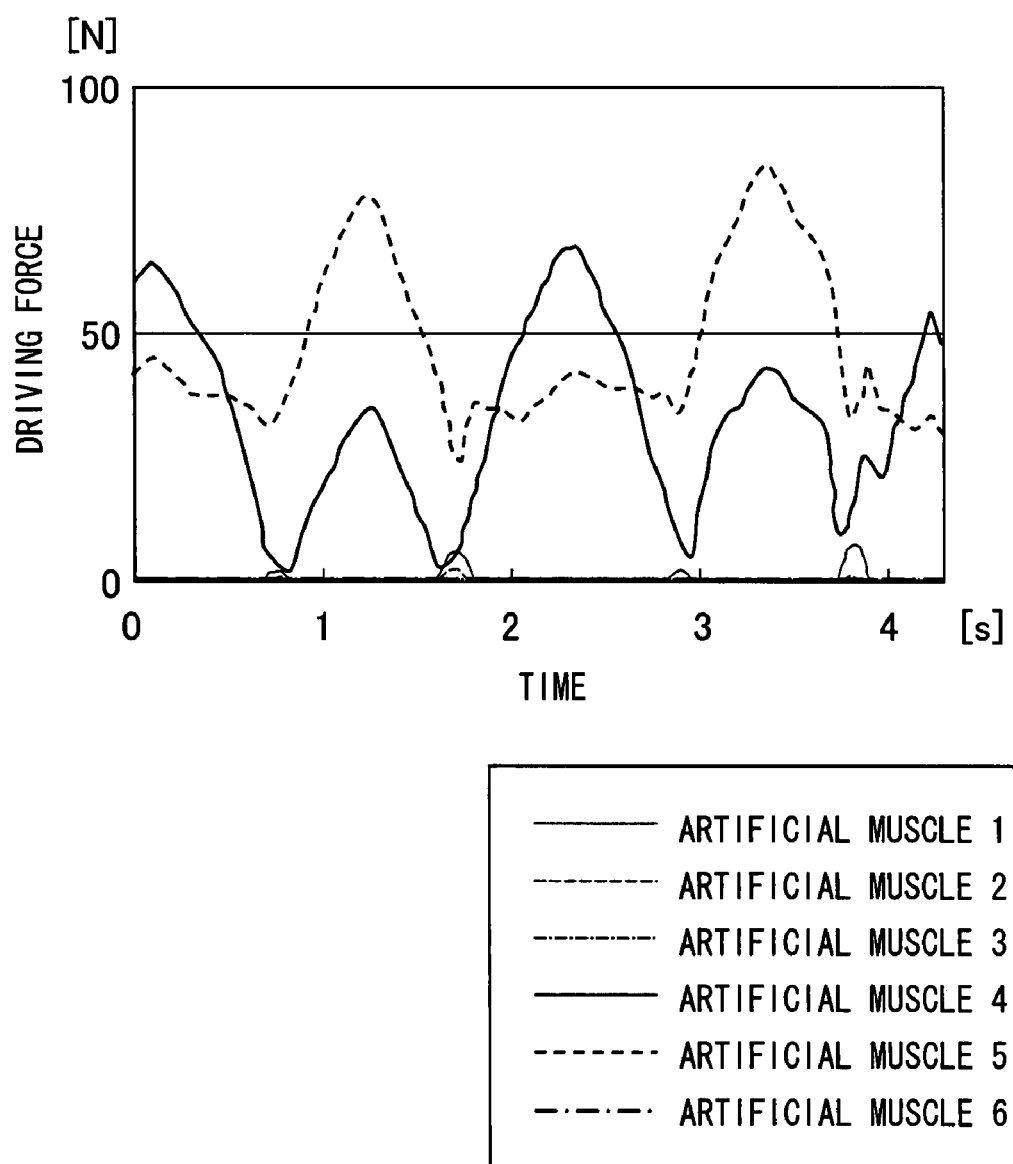

DRIVING FORCE CALCULATING DEVICE, DRIVING FORCE CALCULATING METHOD, POWER ASSISTING DEVICE, PROGRAM, AND COMPUTER-READABLE STORAGE MEDIUM

TECHNICAL FIELD

The present invention relates to: a driving force calculating device for calculating a driving force of a power assisting device that is worn by a living body having bones with a joint and a muscle and that assists and/or resists a rotational motion of the joint with use of the driving section fixed to the bones across the joint; and to a driving force calculating method. Further, the present invention relates to a power assisting device that uses the driving force calculating method or the driving force calculating device.

BACKGROUND ART

In accordance with rapid aging of the population in recent years, there are increasing needs for welfare assistive devices that support caring of aged persons in the field of welfare. The most burdensome work in the field of caring is moving a cared person or adjusting the posture of the cared person. Much attention is paid to care-oriented power assisting devices that alleviate a load applied on the muscle force of a caregiver who makes such movement or adjustment.

For example, Document 1 discloses a care-oriented power assisting device that functions with use of an air pressure actuator having a light weight and a small size. Further, Document 2 discloses a power assisting instrument with a downsized structure that alleviates a load applied on human muscles. Other examples include HAL manufactured by CYBERDYNE Inc.

These power assisting devices are also effective for muscle training with alleviated or added loads on muscles in the field of sports engineering or rehabilitation engineering.

In order to develop a new method for evaluating athletic abilities or a new rehabilitation method, much studies have been made in the field of sports engineering or rehabilitation engineering as to estimation of muscle activities of humans in motion. For example, Document 3 discloses a technique for estimating the muscle force of a living body. In the technique, athletic properties of a subject who operates an exercise device are measured, and inverse analysis is used. Examples of commercially available software for such estimation include "ARMO" that is a 3D muscle simulator manufactured by Gsport Inc., and "SIMM" that is a musculoskeletal model of a whole body manufactured by Musculographics Inc.

It is desirable that a power assisting device worn by a caregiver allows individual regulation of loads applied on respective muscles in consideration of muscular properties, in order that unnatural loads are not applied on the caregiver.

Further, in order to increase a rehabilitation effect for a handicapped person, it is desirable to classify individual muscles into muscles on which loads are to be applied and muscles on which loads are not to be applied, and regulate loads applied on the individual muscles so as to selectively assist the muscles on which loads are not to be applied. Equally, it is desirable to selectively apply loads on the muscles on which loads are to be applied in muscle training.

However, none of Documents 1, 2, and 3 discloses a technique for regulating loads on individual muscles while a power assisting device assists a predetermined motion. For example, the power assisting device disclosed in Document 1 has rotatable joints at positions corresponding to human joints and has actuators for rotating the joints. However, Document 1 does not disclose a method for regulating the driving forces of the actuators so that individual muscles generate respective muscle forces of desired values.

Further, the power assisting instrument disclosed in Document 2 determines the amount of an assist power by causing a sensor section to measure an acting force received by a person when the person acts. However, Document 2 does not disclose a method for regulating individual muscle forces to be generated by respective muscles when determining the amount of assist power. The same can be said about HAL manufactured by CYBERDYNE Inc.

The method disclosed in Document 3 for measuring properties of a muscle force of a living body is a method for measuring properties of a muscle force necessary for a predetermined motion in a case where the person is in a normal state, that is, where the person does not wear a power assisting device. The method is not for controlling the driving force of the power assisting device so that individual muscles generate desired muscle forces in a case where the person wears the power assisting device. The same can be said about "ARMO" that is the 3D muscle simulator manufactured by Gsport Inc., and "SIMM" that is the musculoskeletal model of a whole body manufactured by Musculographics Inc.

[Document 1]
Japanese Unexamined Patent Publication No. 2000-51289 (Tokukai 2000-51289; published on Feb. 22, 2000)
[Document 2]
Japanese Unexamined Patent Publication No. 2004-105261 (Tokukai 2004-105261; published on Apr. 8, 2004)
[Document 3]
Japanese Unexamined Patent Publication No. 1995-313495 (Tokukaihei 7-313495; published on Dec. 5, 1995)

DISCLOSURE OF INVENTION

The present invention was made in view of the foregoing problems. An object of the present invention is to provide a driving force calculating device and a driving force calculating method, each of which allows calculating the driving force of a power assisting device so that a desired load is applied on a muscle while the power assisting device assists and/or resists a predetermined motion.

Another object of the present invention is to provide a power assisting device capable of regulating a load applied on a muscle while a user performs a predetermined motion.

In order to solve the foregoing problems, the driving force calculating device of the present invention is a driving force calculating device for calculating a driving force of a driving section of a power assisting device that is worn by a living body having bones with a joint and a muscle and that assists and/or resists a rotational motion of the joint with use of the driving section fixed to the bones across the joint, the driving force calculating device including: a muscle force input section to which an assigned muscle force that is to be generated in assisting and/or resisting the rotational motion is input; and driving force calculating means for calculating the driving force of the driving section based on the assigned muscle force and on joint torque necessary for the rotational motion, so that the assigned muscle force and the driving force of the driving section generate the joint torque necessary for the rotational motion.

A conventional driving force calculating device calculates a driving force necessary for a rotational motion based only on joint torque necessary for the rotational motion. That is, the conventional driving force calculating device calculates a driving force without considering a load applied on a muscle.

Consequently, the conventional driving force calculating device cannot freely control the load applied on the muscle when a power assisting device is driven with the calculated driving force.

In contrast, with the arrangement of the present invention, the driving force calculating means calculates a driving force based on the assigned muscle force input to the muscular input section and the joint torque necessary for the rotational motion. Consequently, the driving force is calculated in consideration of the assigned muscle force, as well as the driving force is necessary for assisting the rotational motion. Therefore, when driving the power assisting device with the calculated driving force, a muscle to which a muscle force is assigned generates a muscle force in accordance with the assigned muscle force. In this manner, the driving force calculating device can calculate a driving force so that a desired load is applied on a muscle when the power assisting device assists and/or resists a predetermined motion.

In order to solve the foregoing problems, the driving force calculating method of the present invention is a driving force calculating method for calculating a driving force of a driving section of a power assisting device that is worn by a living body having bones with a joint and a muscle and that assists and/or resists a rotational motion of the joint with use of the driving section fixed to the bones across the joint, the driving force calculating method including the steps of: (a) assigning a desired muscle force to the muscle; and (b) calculating the driving force of the driving section based on the muscle force assigned in the step (a) and joint torque necessary for the rotational motion, so that the muscle force assigned in the step (a) and the driving force of the driving section generate the joint torque necessary for the rotational motion.

With the arrangement, the driving force is calculated based on the muscle force assigned in the step (a) (assigned muscle force) and the joint torque necessary for the rotational motion. Consequently, the driving force is calculated in consideration of the assigned muscle force, as well as the driving force is necessary for assisting the rotational motion. Therefore, when driving the power assisting device with the calculated driving force, a muscle to which a muscle force is assigned generates a muscle force in accordance with the assigned muscle force. In this manner, the driving force calculating device can calculate a driving force so that a desired load is applied on a muscle when the power assisting device assists and/or resists a predetermined motion.

The power assisting device of the present invention is a power assisting device, that is worn by a living body having bones with a joint and a muscle and that assists and/or resists a rotational motion of the joint, the power assisting device including: the driving force calculating device as mentioned above; a driving section fixed to the bones of the living body across the joint; and a driving force control section for controlling a driving force of the driving section, the driving force control section controlling the driving force of the driving section based on the driving force calculated by the driving force calculating device.

With the arrangement, the driving force control section controls the driving section based on the driving force calculated by the driving force calculating device. The driving force calculating device can calculate a driving force so that a desired load is applied on a muscle when the power assisting device assists and/or resists a predetermined motion. Therefore, the power assisting device can regulate a load applied on a muscle when a user performs a predetermined motion.

The power assisting device of the present invention is a power assisting device, that is worn by a living body having bones with a joint and a muscle and that assists and/or resists a rotational motion of the joint, the power assisting device including: a storage section for storing data of a driving force calculated through a driving force calculating method as mentioned above; a driving section fixed to the bones of the living body across the joint; and a driving force control section for controlling a driving force of the driving section, the driving force control section controlling the driving section based on the data of the driving force that is stored in the storage section.

With the arrangement, the power assisting device includes the data of the driving force calculated through the driving force calculating method. Consequently, when the driving force control section controls the driving section based on the data of the driving force, the power assisting device can regulate a load applied on a muscle when the user performs a predetermined motion. Further, the power assisting device includes the data of the driving force in advance, and therefore the power assisting device can promptly assist the rotational motion without spending time in calculating the driving force.

Additional objects, features, and strengths of the present invention will be made clear by the description below. Further, the advantages of the present invention will be evident from the following explanation in reference to the drawings.

BRIEF DESCRIPTION OF DRAWINGS

FIG. 10 relates to the example of the present invention and is a graph illustrating a joint torque table.

FIG. 13 relates to the example of the present invention and is a graph illustrating a driving force table.

BEST MODE FOR CARRYING OUT THE INVENTION

Embodiment 1

The following explains an embodiment of the present invention with reference to FIGS. 1 to 5. In the present embodiment, an explanation will be made as to a driving force calculating device 1 that is included in a power assisting device and that calculates the driving force of the power assisting device.

First, an explanation will be made as to the power assisting device whose driving force is to be calculated by the driving force calculating device of the present embodiment. The power assisting device is to be worn by a living body having bones with a joint and a muscle (the living body is a human in the present embodiment). The power assisting device includes a plurality of driving sections (hereinafter also referred to as "artificial muscle") and each of the driving sections is fixed to the bones of the living body (human) across the joint.

Figure 4:
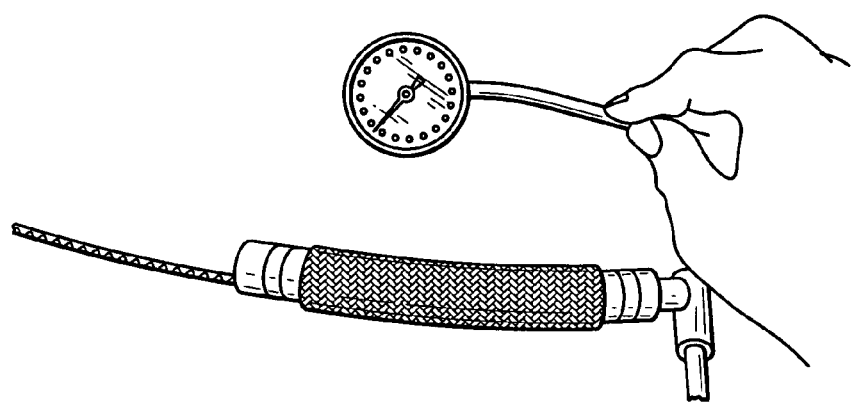
FIG. 4 relates to the embodiment of the present invention and is a drawing illustrating an example of an actuator included in the power assisting device.

The structure of the driving section is not particularly limited. For example, as illustrated in FIG. 4, the driving section may have a shape that models a human muscle, that is, the driving section may be an actuator that can extend and contract in a long direction. More specifically, the driving section may be made of a rubber tube and a carbon wire that covers the rubber tube. In this case, one actuator corresponds to one muscle of the living body, and the driving force of each driving section is in proportion to (i) the pressure of air put into the actuator and (ii) the cross-sectional area of the actuator. That is, in a case where the maximum pressure of air put into each actuator is the same as each other, the maximum driving force of each actuator is in proportion to the cross-sectional area of the rubber tube that is vertical to a direction in which the rubber tube expands and contracts.

When the driving section generates a driving force, the driving force is applied on portions to which the driving section is fixed and which are provided at the front and the back of a joint. Thus, torque is generated at the joint with the joint axis being the center. The power assisting device assists and/or resists a rotational motion of the joint with use of the torque. Examples of assisting a rotational motion include a case of caring and a case of rehabilitation. Examples of resisting a rotational motion include a case of muscle training.

Figure 1:
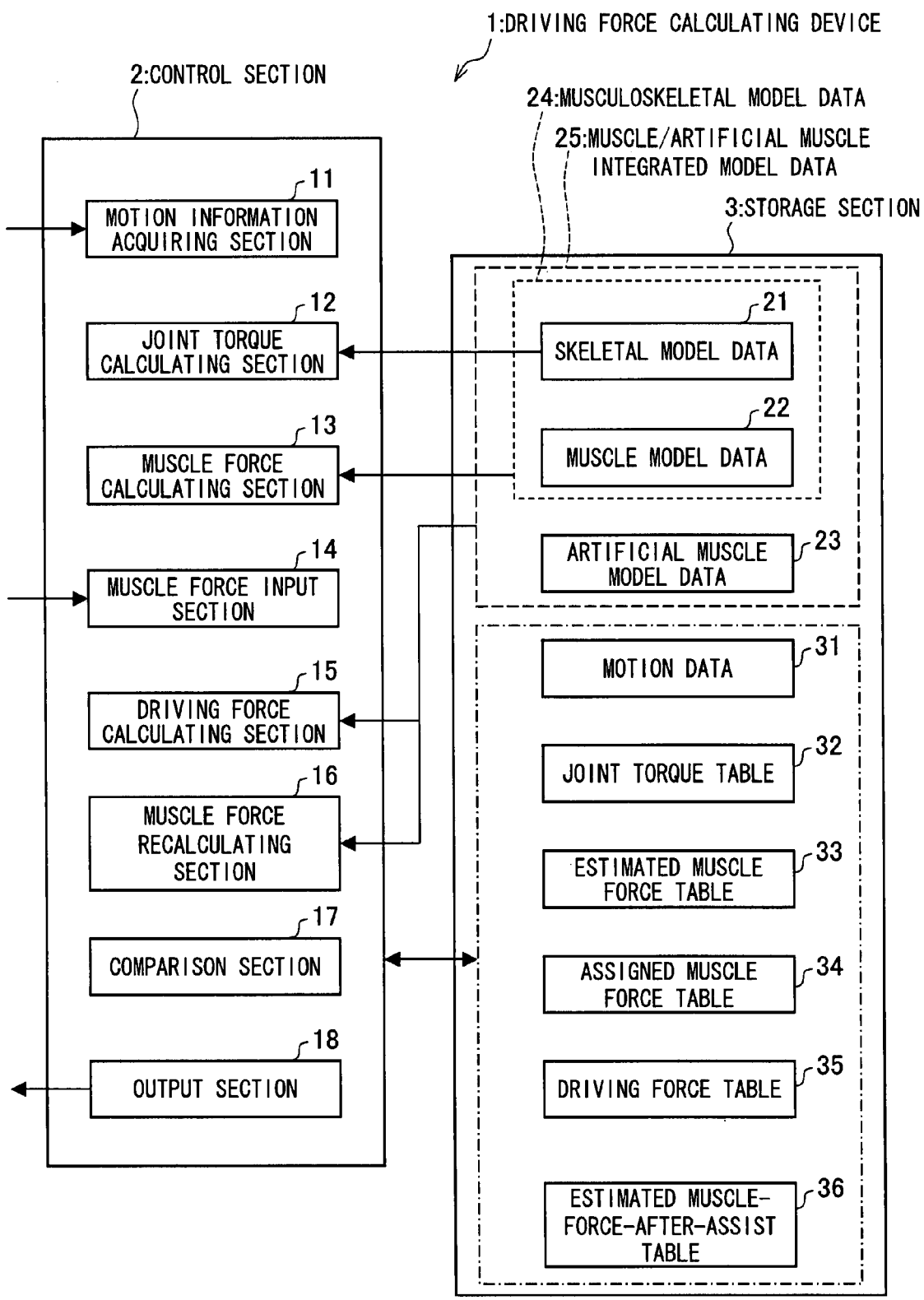
FIG. 1 relates to an embodiment of the present invention and is a block diagram illustrating a main structure of a driving force calculating device.

Next, the following explains the driving force calculating device 1 of the present embodiment. FIG. 1 is a block diagram of the driving force calculating device 1. The driving force calculating device 1 includes a control section 2 and a storage section 3.

The control section 2 includes a CPU, a RAM, and input/output interfaces. The input/output interfaces are not particularly limited. Examples of the input/output interfaces include: an input interface such as a keyboard, a touch panel, a mouse, a detection sensor, and a camera; an output interface such as a display and a printer; and a two-way interface for a reading and recording device etc.

The storage section 3 stores data necessary for later-mentioned processes and data obtained in the processes. The storage section 3 includes an RAM or a HDD for example.

As illustrated in FIG. 1, the control section 2 includes a motion information acquiring section (motion information acquiring means) 11, a joint torque calculating section (joint torque calculating means) 12, a muscle force calculating section (muscle force calculating means) 13, a muscle force input section 14, a driving force calculating section (driving force calculating means) 15, a muscle force recalculating section (muscle force recalculating means) 16, a comparison section (comparison means) 17, and an output section 18.

The motion information acquiring section 11 acquires motion information based on a motion of a living body. In the present embodiment, the motion information acquiring section 11 acquires motion information based on a rotational motion at a joint of a human to be assisted by the power assisting device. The motion information acquiring section 11 acquires information of a rotational motion at each instant based on an actual rotational motion of the joint. Examples of the acquired information include information of the angle of the joint and information of angular velocity and angular acceleration in the rotational motion. The motion information acquiring section 11 is not particularly limited as long as it can acquire motion information of a rotational motion of a joint. For example, the motion information acquiring section 11 may acquire images of a rotational motion with use of a camera and extract motion information, or may detect the rotational motion with use of a sensor and extract the motion information. Specifically, the motion information acquiring section 11 may be a so-called motion capture device or may be a device using a force plate or an accelerometer. Alternatively, the motion information acquiring section 11 may take in image data etc. that has been acquired beforehand and extract motion information from the image data. Further, the motion information acquiring section 11 may receive already-acquired motion information without changing the information. It is preferable that the motion information acquiring section 11 can acquire motion information of a plurality of joints based on an actual rotational motion at once.

The joint torque calculating section 12 calculates joint torque necessary for a rotational motion, the calculation being performed with respect to each joint. The joint torque means torque for rotating a joint.

The muscle force calculating section 13 calculates a muscle force necessary for rotating a joint in a state where a person does not wear the power assisting device. The muscle force is calculated based on the joint torque necessary for a rotational motion with respect to each joint. The joint torque used in calculating the muscle force is the torque calculated by the joint torque calculating section 12.

To the muscle force input section 14 is input an assigned muscle force that is a muscle force assigned to a muscle. Examples of the muscle force input section 14 include: an input interface such as a keyboard, a mouse, and a touch panel; and an input/output interface for an external device such as a HDD and a network connecting section.

The assigned muscle force input via the muscle force input section 14 may be a specific value of a muscle force or may be a ratio etc. to the muscle force that has been calculated by the muscle force calculating section 13. The latter case will be detailed later. A muscle force may be assigned to a single muscle. However, the present embodiment is arranged in the preferable manner so that desired muscle forces can be assigned to respective desired muscles. Therefore, information of a muscle to which a muscle force is assigned and information of the muscle force to be assigned to the muscle are input to the muscle force input section 14.

The driving force calculating section 15 calculates a driving force of the driving section based on (i) the assigned muscle force input via the muscle force input section 14 and (ii) the joint torque necessary for a rotational motion. In the present embodiment, the driving force calculating section 15 calculates a driving force based on muscles to which respective muscle forces are assigned and the muscle forces. The joint torque used in calculating the driving force is calculated by the joint torque calculating section 12.

The muscle force recalculating section 16 calculates a muscle force necessary for the rotational motion, based on the driving force calculated by the driving force calculating section 15 and the joint torque necessary for the rotational motion. The joint torque used in calculating the muscle force is calculated by the joint torque calculating section 12.

The comparison section 17 compares the muscle force calculated by the muscle force recalculating section 16 with the assigned muscle force input via the muscle force input section 14.

The output section 18 transmits data of the calculated driving force to the outside. Examples of the output section 18 include: an output interface such as a display and a printer; and a two-way interface for a reading and recording device etc.

As illustrated in FIG. 1, the storage section 3 stores skeletal model data 21, muscle model data 22, and artificial muscle model data 23 beforehand. Further, the storage section 3 is capable of storing motion data 31, a joint torque table 32, an estimated muscle force table 33, an assigned muscle force table 34, a driving force table 35, and an estimated muscle-force-after-assist table 36.

The skeletal model data 21 includes three-dimensional structural information regarding bones of a living body (human). Specifically, the skeletal model data 21 includes information of the length of each bone, information of the size of each bone, information of spatial arrangement of each bone, information of the weight of each bone, information of moment of inertia of each bone, and information of relative position of a joint axis. In the present embodiment, the skeletal model data 21 is a link model in which multiple bones are linked via joints that rotate with fixed joint axes being centers. However, the present invention is not limited to this. The skeletal model data 21 may be a model in which a joint axis moves relative to a joint in accordance with a rotation of the joint. In this case, by adding a short virtual link to a joint portion, it is possible to reproduce a skeleton in which a joint axis moves, e.g., a skeleton of a human. The skeleton used in the skeletal model data may be that of a whole body, or may be that of a part of a body, such as an upper limb and a lower limb. Using the skeletal model data 21, it is possible to reproduce a skeleton model of a human.

The muscle model data 22 includes three-dimensional structural information regarding muscles of a living body (human). Specifically, the muscle model data 22 includes information of the length of each muscle and information of the position where each muscle attaches to bones. In this manner, each muscle is modeled as a weightless wire. The muscle model data 22 is combined with the skeletal model data 21, so that musculoskeletal model data 24 is obtained. The musculoskeletal model data 24 allows reproduction of a musculoskeletal model in which muscles are superimposed on the bones of a human. The muscle model data 22 further includes information of physiological cross-sectional area of each muscle. The muscle model data 22 may further include information of the mass of each muscle and/or information of moment of inertia of each muscle etc. When the muscle model data 22 includes the information of the mass of each muscle and the information of moment of inertia of each muscle, the reproduced musculoskeletal model gets closer to actual bones and muscles.

The artificial muscle model data 23 includes three-dimensional structural information regarding the driving section of the power assisting device. Specifically, the artificial muscle model data 23 includes information of the length of the driving section and information of the position where an end of the driving section attaches to a bone when a human wears the power assisting device. This allows the driving section to be modeled as a weightless wire. The artificial muscle model data 23 is combined with the musculoskeletal model data 24, so that a muscle/artificial muscle integrated model data 25 is obtained. The muscle/artificial muscle integrated model data 25 allows reproduction of a muscle/artificial muscle integrated model in which muscles and driving sections are superimposed on the bones of a human. The artificial muscle model data 23 further includes information of the cross-sectional area that is vertical to a direction in which the driving section expands and contracts. In the present embodiment, the maximum driving force can be obtained from the information of the cross-sectional area. The artificial muscle model data 23 may include information of the maximum driving force instead of the information of the cross-sectional area. The artificial muscle model data 23 may further include information of the mass of each driving section and/or information of moment of inertia of each driving section etc.

The motion data 31 includes motion information acquired by the motion information acquiring section 11. Specifically, the motion data 31 includes information of the angle of a joint, information of the angular velocity of the joint, and information of the angular acceleration of the joint at each instant in a rotational motion. Therefore, the motion data 31 is a table between time and the angle, the angular velocity, and the angular acceleration.

The joint torque table 32 includes information of joint torque which is necessary for a rotational motion of a joint and which has been calculated by the joint torque calculating section 12. Specifically, the joint torque table 32 includes information of joint torque which is necessary at each instant in the rotational motion. Therefore, the joint torque table 32 is a table indicative of relation between time and joint torque.

The estimated muscle force table 33 includes information of a muscle force necessary for a rotational motion of a joint in a case where there is no assist from the power assisting device. The muscle force has been calculated by the muscle force calculating section 13. Specifically, the estimated muscle force table 33 includes information of a muscle force necessary at each instant in the rotational motion. Therefore, the estimated muscle force table 33 is a table indicative of relation between time and a muscle force.

The assigned muscle force table 34 includes information of an assigned muscle force having been input via the muscle force input section 14. Specifically, the assigned muscle force table 34 includes information of an assigned muscle force at each instant in the rotational motion. Therefore, the assigned muscle force table 34 indicates relation between time and an assigned muscle force.

The driving force table 35 includes information of a driving force of the driving section of the power assisting device. The driving force has been calculated by the driving force calculating section 15. Specifically, the driving force table 35 includes information of a driving force necessary at each instant in the rotational motion. Therefore, the driving force table 35 is a table indicative of relation between time and a driving force.

The estimated muscle-force-after-assist table 36 includes information of a muscle force necessary for the rotational motion at a time when the driving section is driven based on the driving force table 35 so as to assist the rotational motion. Specifically, the estimated muscle-force-after-assist table 36 includes information of a muscle force necessary at each instant in the rotational motion. Therefore, the estimated muscle-force-after-assist table 36 indicates relation between time and a muscle force. The estimated muscle-force-after-assist table 36 stores values calculated by the muscle force recalculating section 16.

Figure 2:
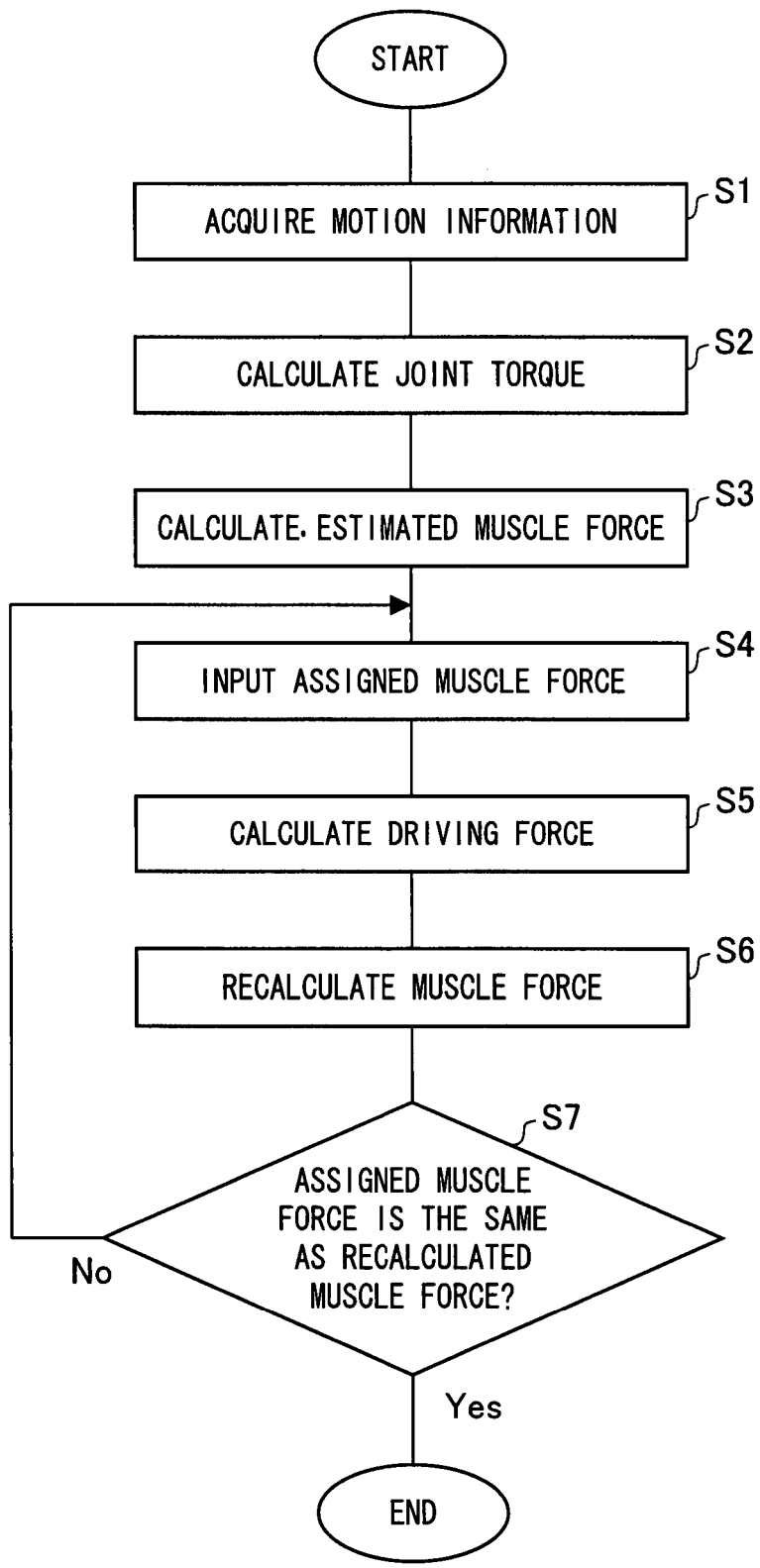
FIG. 2 relates to the embodiment of the present invention and is a flowchart illustrating processing steps of the driving force calculating device.

The following explains performance of the driving force calculating device. FIG. 2 is a process chart of the muscle force calculation method of the present embodiment.

First, a subject performs a rotational motion of a joint. The motion information acquiring section 11 acquires the rotational motion with use of a camera etc., and extracts motion information from the acquired image information (step S1). When extracting the motion information from the image information, the skeletal model data 21 in the storage section 3 may be used in order to specify the position of a joint or bones in the image information. Further, the motion information is acquired at a plurality of instants from the beginning of the rotational motion to the end of the rotational motion. Examples of the acquired motion information include the angle of a joint, the angular velocity of the joint, and the angular acceleration of the joint at each instant. The acquired motion information is converted into a table indicative of relation between time and the angle, the angular velocity, and the angular acceleration, and the table is stored as the motion data 31 in the storage section 3.

Next, the joint torque calculating section 12 calculates, with respect to each joint, joint torque necessary for the rotational motion, based on the motion data 31 stored in the storage section 3 (step S2). Specifically, the joint torque calculating section 12 calculates joint torque for allowing the rotational motion, based on (i) the angle of a joint, the angular velocity of the joint, and the angular acceleration of the joint included in the motion data 31, (ii) gravitational acceleration, and (iii) mass and moment of inertia applied on a bone included in the skeletal model data 21, with use of dynamics calculations such as Newton-Euler method and Lagrange method. The joint torque is calculated with respect to each instant. The joint torque calculated for each joint is caused to be associated with time, and stored as the joint torque table 32 in the storage section 3.

Subsequently, the muscle force calculating section 13 calculates a muscle force necessary for the rotational motion at a time when the subject does not wear the power assisting device (step S3). The calculated muscle force is used for subsequently assigning muscle forces. Specifically, the muscle force calculating section 13 calculates a muscle force of each necessary muscle, based on the musculoskeletal model data 24 and the joint torque table 32 stored in the storage section 3. The muscle force is calculated for each instant, and the obtained muscle force (estimated muscle force) is caused to be associated with time, and stored as the estimated muscle force table 33 in the storage section 3.

The following details the method for calculating the estimated muscle force. It is assumed that joint i represents each joint, j number of muscles are across the joint i, $r_j$ is moment arm of the muscle j (distance between the joint axis of the joint i and a point to which the muscle j attaches across joint i), and $f_j$ represents the muscle force of the muscle j. At that time, torque $\tau_i$ at joint i is represented by an equation as presented below.

$$\tau_i = \sum_j r_j \times f_j \quad (1)$$

Here, torque $\tau_i$ has been calculated by the joint torque calculating section 12 and is stored as joint torque data in the storage section 3. Further, $r_j$ can be calculated from the musculoskeletal model data 24. Accordingly, $\tau_i$ and $r_j$ in Equation (1) are substituted with the numerical values. However, $f_j$ represents a plurality of parameters, it is impossible to determine the numerical value for each $f_j$.

Here, in order to determine the numerical value of $f_j$, the present embodiment uses optimization calculation proposed by Crowninshield. That is, when a human performs a certain motion, muscle forces are distributed to muscle forces $f_j$ of respective muscles so that performance function u(f) as presented below has the minimum value $$u(f) = \sum_{j=1}^{n} \left(\frac{f_j}{A_j}\right)^2 \quad (2)$$

where n is the number of muscles and $A_j$ is the physiological cross-sectional area of the muscle j. With use of Equation (2), muscle forces are distributed so that the sum of a square of a muscle force per unit cross-sectional area of each muscle has the minimum value.

The muscle force calculating section 13 optimizes $f_j$ so that Equation (2) has the minimum value. In this case, muscle force $f_j$ is calculated so that Equation (2) has the minimum value under the condition that torque $\tau_i$ stored in the joint torque table 32, moment arm $r_j$ calculated from the musculoskeletal model data 24, and muscle forces $f_j$ satisfy Equation (1). In other words, the muscle force calculating section 13 calculates $f_j$ so that Equation (2) has the minimum value under the constraint conditions of torque $\tau_i$ and $r_j$ in Equation (1). The value of physiological cross-sectional area $A_j$ necessary for the optimization calculation of $f_j$ is included in the muscle model data 22.

A further constraint condition may be added in the optimization calculation using Equation (2). For example, it is known that muscle force $f_j$ that can be generated by a muscle is in a range represented by Inequality (3) as presented below $$0 \leq f_j \leq kA_j \quad (3)$$

where $k=0.7\times10^6 [N/m^2]$ and $A_j$ is the physiological cross-sectional area of muscle j. Therefore, it is preferable to use Inequality (3) as the further constraint condition. This allows excluding a muscle force that cannot be actually generated by a muscle of a living body.

With the optimization calculation, muscle force $f_j$ of each muscle is calculated. The muscle force calculating section 13 performs the calculation with respect to each instant in the rotational motion. The muscle force of each muscle thus obtained is stored in the storage section 3 as the estimated muscle force table 33 indicative of relation between time and the muscle force.

Subsequently, information of a muscle to which a muscle force is to be assigned and information of the muscle force to be assigned to the muscle are input via the muscle force input section 14 (step S4). Here, for assigning the muscle force, a desired muscle force may be input in the form of any waveform. Alternatively, the muscle force may be assigned by using a ratio of a desired muscle force to the muscle force stored in the estimated muscle force table 33. In the latter case, a muscle force can be assigned in the form of a desired ratio to a muscle force necessary for a certain motion. This allows a user to easily assign the amount of assist from the power assisting device.

In the case of assigning a muscle force with use of the ratio, information of a muscle to which a muscle force is to be assigned and the ratio indicative of the muscle force to be assigned to the muscle are input to the muscle force input section 14. The muscle force input section 14 refers to the estimated muscle force table 33 and thus extracts muscle force data of the muscle to which the muscle force is to be assigned, and the muscle force input section 14 multiplies the extracted muscle force data by the input ratio. The muscle force obtained by the multiplication is regarded as an assigned muscle force, and is stored in the storage section 3 as the assigned muscle force table 34 indicative of relation between time and the assigned muscle force.

Subsequently, the driving force calculating section 15 calculates a driving force to be generated by the driving section in the rotational motion, based on the muscle force input to the muscle force input section 14 (step S5). Here, the driving force calculating section 15 uses the muscle/artificial muscle integrated model data 25 integrally including the musculoskeletal model data 24 and the artificial muscle model data 23. Specifically, the driving force calculating section 15 extends the definition of the muscle forces of the muscles in Equations (1) and (2) to include the muscle forces of the muscles and the driving forces of the driving sections. Then, $f_j$ is optimized with use of Equation (1) under the constraint conditions of joint torque and the assigned muscle force. Thus, $f_j$ is calculated.

Specifically, torque $\tau_i$ at joint i is represented by an equation:

$$\tau_i = \sum_j r_j \times f_j \qquad (4)$$

where i is the numerical order of a joint, ii is joint torque at joint i, j is the numerical order of a muscle or a driving section that is across joint i, $r_j$ is moment arm of the muscle j or the driving section j, and $f_j$ is a muscle force of the muscle j or a driving force of the driving section j. Here, torque $\tau_i$ can be obtained by referring to the joint torque table 32 stored in the storage section 3, and moment arm $r_j$ can be calculated from the muscle/artificial muscle integrated model data 25. Further, out of $f_j$, numerical value of muscle force $f_j$ of the muscle to which the muscle force has been assigned is obtained from the assigned muscle force table 34.

Under the condition that muscle forces $f_j$ of muscles to which muscle forces have not been assigned and driving forces $f_j$ of the driving sections satisfy Equation (4), $f_j$ is calculated so that performance function u(f) as presented below has the minimum value $$u(f) = \sum_{j=1}^{n} \left(\frac{f_j}{A_j}\right)^2 \qquad (5)$$

where n is the sum of (i) the number of a muscle to which a muscle force has not been assigned by the muscle force input section and (ii) the number of a driving section, j is the numerical order of the muscle to which a muscle force has not been assigned by the muscle force input section or the numerical order of the driving section, $f_j$ is the muscle force of the j-th muscle or the driving force of the j-th driving section, and $A_j$ is physiological cross-sectional area of a muscle in a case where j represents the muscle, and $A_j$ is a value based on the maximum driving force of the driving section in a case where j represents the driving section. A suitable value based on the experimental result may be assigned to $A_j$ in the case where j represents the driving section. It is preferable that $A_j$ is in proportion to the maximum driving force of the driving section j. In the present embodiment, the maximum driving force of the driving section is in proportion to the cross-sectional area of the driving section, and accordingly the cross-sectional area of the driving section is used as $A_j$. Of course, the maximum driving force may be used as $A_j$ instead of the cross-sectional area of the driving section. Further, it is preferable that Inequality (3) is further added as the constraint condition in this process of calculating $f_j$.

With the optimization calculation, $f_j$ that is a muscle force of a muscle to which a muscle force has not been assigned and that is a driving force of each driving section is calculated. The driving force calculating section 15 performs the calculation with respect to each instant in the rotational motion. The driving force thus obtained of each driving section is stored in the storage section 3 as the driving force table 35 indicative of relation between time and the driving force.

Subsequently, the muscle force recalculating section 16 calculates a muscle force to be generated by a muscle in a case where the power assisting device assists a rotational motion of a joint with use of data of the driving force stored in the driving force table 35 (step S6). At this time, the muscle force recalculating section 16 uses, as the constraint condition, the driving force of the driving section instead of the assigned muscle force.

That is, under the constraint condition of Equation (4) and data of the driving force of the driving section that is stored in the driving force table 35, muscle force $f_j$ is calculated so that performance function u(f) as presented below has the minimum value $$u(f) = \sum_{j=1}^{n} \left(\frac{f_j}{A_j}\right)^2 \qquad (6)$$

where n is the number of muscles, j is the numerical order of a muscle, $f_j$ is the muscle force of muscle j, and $A_j$ is physiological cross-sectional area of muscle j. It is preferable that Inequality (3) is further added as the constraint condition in this process of calculating $f_j$.

With the optimization calculation, muscle forces $f_j$ of all muscles at a time when the power assisting device assists the rotational motion are calculated. The muscle force recalculating section 16 performs the calculation with respect to each instant in the rotational motion. The muscle force thus obtained is stored in the storage section 3 as the estimated muscle-force-after-assist table 36 indicative of relation between time and the estimated muscle force after assist.

Subsequently, the comparison section 17 compares (i) the muscle force at the time of the assist, which is calculated by the muscle force recalculating section 16, with (ii) the assigned muscle force that has been assigned by the muscle force input section 14, so as to check whether a difference exists between the two muscle forces (step S7). Specifically, the comparison section 17 compares the assigned muscle force table 34 with the estimated muscle-force-after-assist table 36. When the muscle force at the time of the assist is substantially the same as the assigned muscle force, all processes are finished. On the other hand, when the two muscle forces are different from each other, it appears that the assigned muscle force is inappropriate. Therefore, the process goes back to step S4 and a muscle force is input again.

Note that, the condition for finishing all the processes is not limited to a complete correspondence between the muscle force at the time of the assist and the assigned muscle force.

For example, all the processes may be finished when the muscle force at the time of the assist is in a range of the assigned muscle force±A %. In this case, A % may be assigned according to the purpose of the power assisting device.

As described above, the driving force calculating device 1 of the present embodiment is constructed such that the driving force calculating section 15 calculates the driving force of the driving section under the constraint condition of the assigned muscle force. Consequently, by driving the driving section with use of the calculated driving force, it is possible to assist the rotational motion so that the muscle to which a muscle force has been assigned has the assigned muscle force.

Note that, in the above performance functions (2), (5), and (6), the sum of a square of $f_j/A_j$ was used for the evaluation. Alternatively, the sum of a third power of $f_j/A_j$ or the sum of a hundred power of $f_j/A_j$ may be used for the evaluation. That is, the sum of m power (m is an integer of two or more) of a muscle force per unit cross-sectional area of each muscle may be used for the evaluation.

The following explains a power assisting device 100 which includes the driving force calculating device 1. In the power assisting device 100, driving sections are driven in accordance with driving forces calculated by the driving force calculating device 1. The power assisting device 100 of the present embodiment includes the driving force calculating device 1, a plurality of driving sections 101, and a driving force control section 102.

Figure 15:
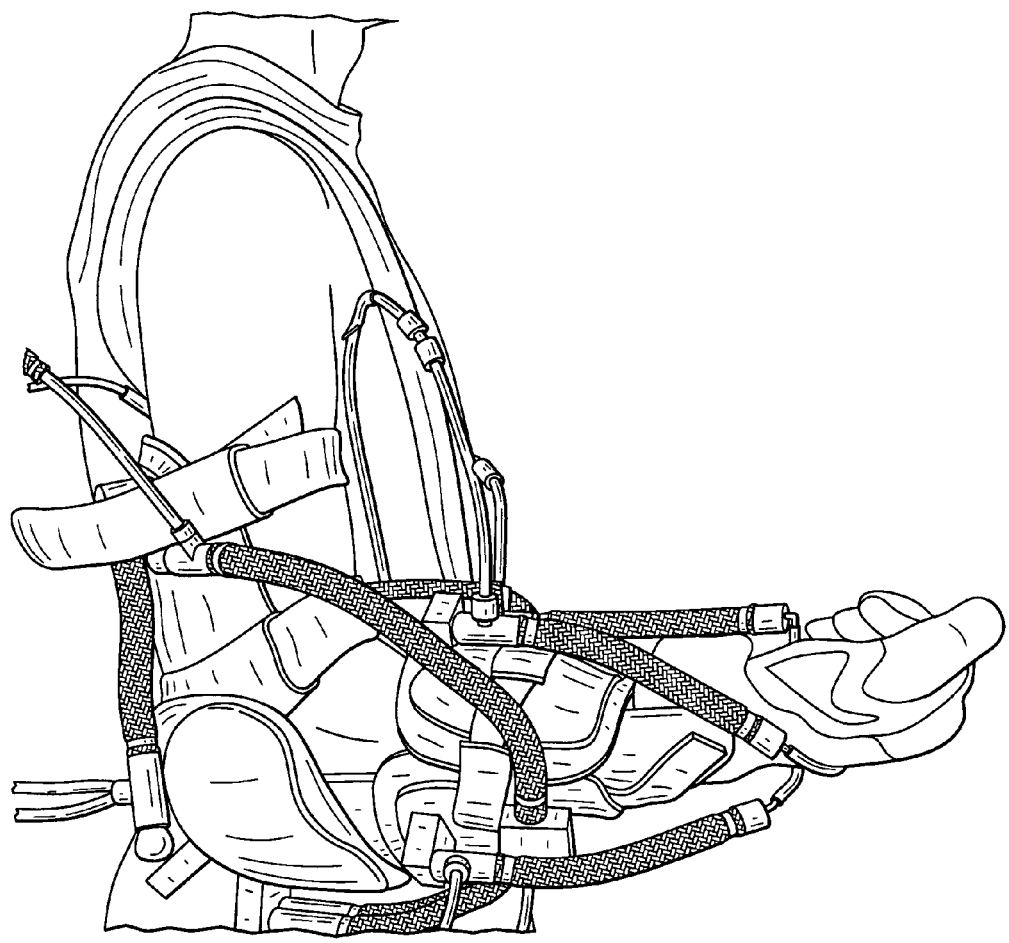
FIG. 15 relates to the embodiment of the present invention and is an outline drawing illustrating a main structure of the power assisting device.

The power assisting device 100 is worn by a living body (human) having bones with a joint and a muscle. Each of the driving sections 101 is fixed to bones of the living body (human) across the joint. Each driving section 101 is fixed to a human body by a supporter, a tape, or the like. FIG. 15 shows an example of the power assisting device 100. However, the present invention is not limited to this example.

The structure of each driving section 101 is not particularly limited. For example, the driving section 101 has a shape that models a human muscle, that is, the driving section 101 may be an actuator having a bar shape that can extend and contract. The driving section 101 may be, for example, an artificial pneumatic rubber muscle with elastic fiber composite as illustrated in FIG. 4.

Figure 3:
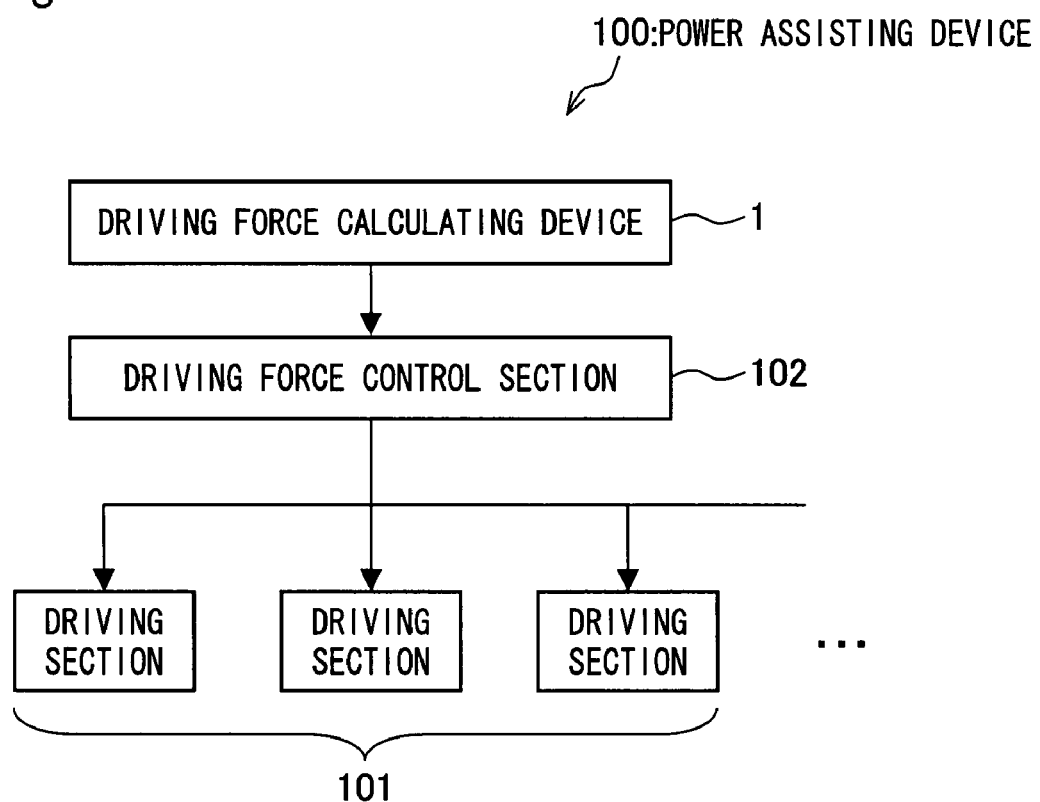
FIG. 3 relates to the embodiment of the present invention and is a block diagram illustrating a main structure of a power assisting device.

FIG. 3 is a functional block diagram of the power assisting device 100. After a muscle force assigned to a muscle on which a reduced or increased load is to be applied is input to the driving force calculating device 1 of the power assisting device 100, a human wearing the power assisting device 100 performs a motion to be assisted by the power assisting device 100. In response to the motion, the driving force calculating device 1 calculates a driving force for assisting the motion. Then, the driving force control section 102 drives each of the driving sections 101 in accordance with the calculated driving force. Each of the driving sections 101 generates a driving force, which is applied to portions to which the driving section 101 is fixed and which are provided at the front and the back of a joint. This generates torque at the joint with the joint axis being the center. Thus, the power assisting device 100 can assist the rotational motion.

The power assisting device 100 of the present embodiment includes the driving force calculating device 1. Accordingly, when assisting the rotational motion, the power assisting device 100 can control muscle forces of respective muscles of the human wearing the power assisting device 100.

In the above embodiment, an explanation was made as to a case where each of members included in the driving force calculating device 1 is "a functional block realized by computing means such as CPU executing a program code stored in a storage medium such as ROM or RAM". Alternatively, the driving force calculating device 1 may be realized by hardware executing the same process. Further, the driving force calculating device 1 can be realized by a combination of hardware carrying out some of the processes and the computing means controlling the hardware and executing program code for the other processes. Further, those members which were described as hardware may be realized by a combination of hardware carrying out some of the processes and the computing means controlling the hardware and executing program code for the other processes. The computing means may be a single entity, or a set of computing means connected over internal device bus and various communications paths may work together to execute program code. Further, out of the members, the storage section 3 may be a storing device itself such as a memory.

The program code itself directly executable by the computing means or the program as data that can generate program code by decompression or an other process (detailed later) is executed by the computing means after the program (program code or the data) is stored and distributed on a storage medium or the program is transmitted and distributed over communications means which transmits the program over wired or wireless communications paths.

To transmit over a communications path, a program is transmitted through the communications path by means of a series of signals indicative of a program which propagate through the transmission media constituting the communications path. To transmit a series of signals, a transmitter device may modulate a carrier wave with the series of signals indicative of the program to transmit the series of signals on the carrier wave. In this case, a receiver device will restore the series of signals by demodulating the carrier wave. Meanwhile, when transmitting the series of signals, the transmitter device may divide the series of signals as a series of digital data into packets for a transmission. In this case, the receiver device will combine received group of packets to restore the series of signals. In addition, the transmitter device may transmit the series of signals by time division, frequency division, code division, or another multiplex scheme involving the series of signals and another series of signals. When this is the case, the receiver device will extract individual series of signals from a multiplex series of signals to restore them. In any case, similar effects are obtained if the program can be transmitted over a communications path.

Here, the storage medium for the distribution of a program is preferably removable. After the distribution of the program, the storage medium may or may not be removable. In addition, the storage medium may or may not be rewritable (writable) or volatile, be recordable by any method, and come in any shape at all, provided that the medium can hold the program. Examples of such a storage medium include tapes, such as magnetism tapes and cassette tapes; magnetic discs, such as floppy (registered trademark) discs and hard discs; and other discs, such as CD-ROMs, magneto-optical discs (MOs), MiniDiscs (MDs), and digital versatile discs (DVDs). In addition, the storage medium may be a card, such as an IC card or an optical card; a semiconductor memory, such as a mask ROM, an EPROM, an EEPROM, or a flash ROM; or a memory provided inside a CPU or other computing means.

The program code may be such that it instructs the computing means regarding all the procedures of the processes. If there is already a basic computer program (for example, an operating system or library) which can be retrieved by a predetermined procedure to execute all or some of the processes, code or a pointer which instructs the computing means to retrieve that basic computer program can replace all or some of the processes.

In addition, the program storage format of the storage medium may be, for example, such that: the computing means can access the program for an execution as in an actual memory having loaded the program; the program is not loaded into an actual memory, but installed in a local storage medium (for example, an actual memory or hard disc) always accessible to the computing means; or the program is stored before installing in a local storage medium from a network or a mobile storage medium. In addition, the program is not limited to compiled object code. The program may be stored as source code or intermediate code generated in the course of interpretation or compilation. In any case, similar effects are obtained regardless of the format in which the storage medium stores the program, provided that decompression of compressed information, decoding of encoded information, interpretation, compilation, links, or loading to an actual memory or combinations of these processes can convert into a format executable by the computing means.

Embodiment 2

Figure 5:
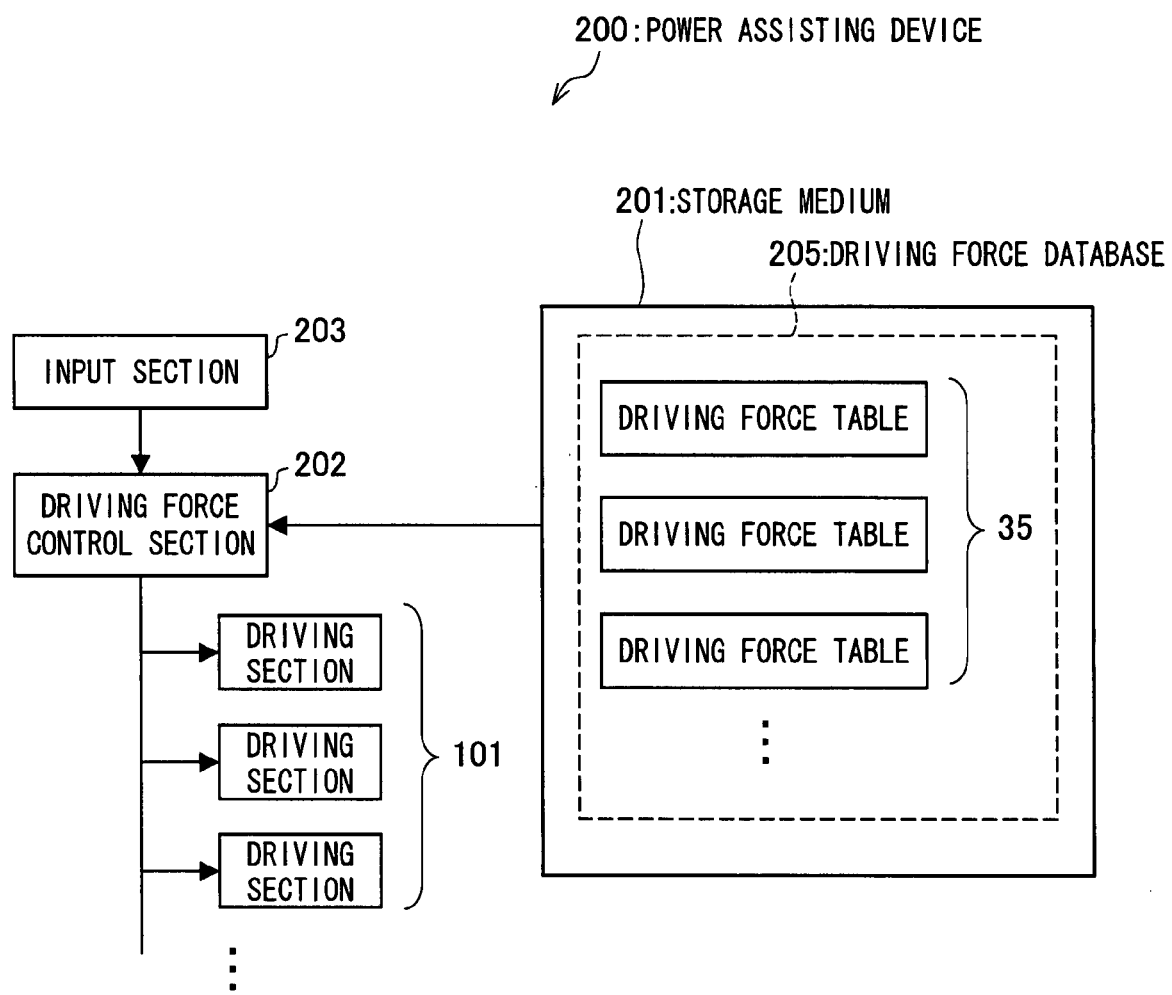
FIG. 5 relates to another embodiment of the present invention and is a block diagram illustrating a main structure of a power assisting device.

The following explains another embodiment of the present invention with reference to FIG. 5. Note that, members having the same functions as those in Embodiment 1 are given the same reference numerals and explanations thereof will be omitted here.

A power assisting device 200 of the present embodiment is worn by a human in the same manner as the power assisting device 100 of Embodiment 1. The power assisting device 200 is different from the power assisting device 100 in that the power assisting device 200 includes a storage medium 201 and a driving force control section 202 instead of the driving force calculating device 1 and the driving force control section 102, respectively, and the power assisting device 200 further includes an input section 203. FIG. 5 is a functional block diagram of the power assisting device 200 of the present embodiment.

The storage medium 201 is a computer-readable storage medium. Specifically, the storage medium 201 may be of the same kind as the storage medium for storing the program in Embodiment 1. The storage medium 201 includes a driving force database 205 including a plurality of driving force tables 35.

Each of the driving force tables 35 has been calculated by the driving force calculating device 1 of Embodiment 1, and is the same as the driving force table 35 of Embodiment 1. The driving force tables 35 have been calculated from different assigned muscle forces, and the driving force tables 35 are stored in the driving force database 205 in such a manner that the driving force tables 35 are associated with respective assigned muscle forces. That is, the driving force database 205 is a database from which the driving force table 35 related to an assigned muscle force that is desired can be obtained.

To the input section 203 is input information of an assigned muscle force which is applied during assisting a predetermined rotational motion. The information of the assigned muscle force to be input to the input section 203 is selected from options for a plurality of assigned muscle forces that have been provided beforehand. This allows a user of the power assisting device to easily specify the assigned muscle force.

The driving force control section 202 is a computer which includes CPU, RAM, and a reader for the storage medium 201, and which is capable of reading information from the storage medium 201. In accordance with the information of the assigned muscle force input to the input section 203, the driving force control section 202 reads out, from the storage medium 201, the driving force table 35 corresponding to the input assigned muscle force. The driving force control section 202 controls driving forces of the driving sections 101 in accordance with driving force data included in the driving force table 35 thus read out.

For example, one of the driving force tables 35, which is used in assisting a predetermined motion, is associated with an assigned muscle force that is 150% with respect to a muscle force calculated by the muscle force calculating section (estimated muscle force). Another one of the driving force tables 35, which is used in assisting the same motion, is associated with an assigned muscle force that is 200% with respect to the estimated muscle force. These driving force tables 35 are stored in the driving force database 205 in such a manner that the driving force tables 35 are associated with information of respective assigned muscle forces. Accordingly, the driving force control section 202 can retrieve, from the driving force database 205, the driving force table 35 that is associated with information of the assigned muscle force input to the input section 203. For example, when information indicative of an assigned muscle force being 150% is input to the input section 203, the driving force control section 202 retrieves, from the plurality of driving force tables 35, the driving force table 35 corresponding to the assigned muscle force being 150%, and drives the driving sections 101 in accordance with driving force data included in the driving force table 35 thus retrieved. Consequently, the power assisting device 200 generates a driving force so that the muscle force of the user increases by 150% compared with a case where the user does not wear the power assisting device.

An explanation was made above as to a case where information input to the input section 203 is only information of an assigned muscle force. However, the present invention is not limited to this case. It is preferable to arrange the present invention so that information for specifying a motion to be assisted and information for specifying a muscle to which a muscle force is to be assigned are further input to the input section 203.

In that case, each of the driving force tables 35 is stored in the driving force database 205 in such a manner that each driving force table 35 is associated with the information for specifying a motion to be assisted and the information for specifying a muscle to which a muscle force is to be assigned, as well as the information of an assigned muscle force. After the information for specifying a motion to be assisted, the information for specifying a muscle to which a muscle force is to be assigned, and the assigned muscle force are input to the input section 203, the driving force control section 202 retrieves, from the driving force database 205, the driving force table 35 corresponding to the three sets of information, and controls driving forces of the driving sections 101 in accordance with the driving force table 35 thus retrieved.

The information of a motion to be assisted, which is input to the input section 203, may be information indicative of options for a plurality of motions that have been provided beforehand, or other information. Alternatively, the motion of the user is detected by a motion capture device or a sensor attached to a joint, and the detected motion is input to the input section 203 as the motion to be assisted.

As described above, the power assisting device 200 of the present embodiment includes, in the driving force database 205 beforehand, the driving force tables 35 associated with various driving conditions such as a motion to be assisted, a muscle to which a muscle force is to be assigned, and an assigned muscle force to be assigned to the muscle. Therefore, there is no need to make a complex calculation. This allows prompt assist of a motion.

An explanation was made above as to a case where the driving force database 205 is stored in the storage medium 201. Alternatively, the driving force database 205 may be stored in a storing member such as RAM or ROM.

Examples

The following explains an example of the present invention with reference to FIGS. 6 to 14. The present invention is not limited to this example.

(Musculoskeletal Model and Muscle/Artificial Muscle Integrated Model)

Figure 6:
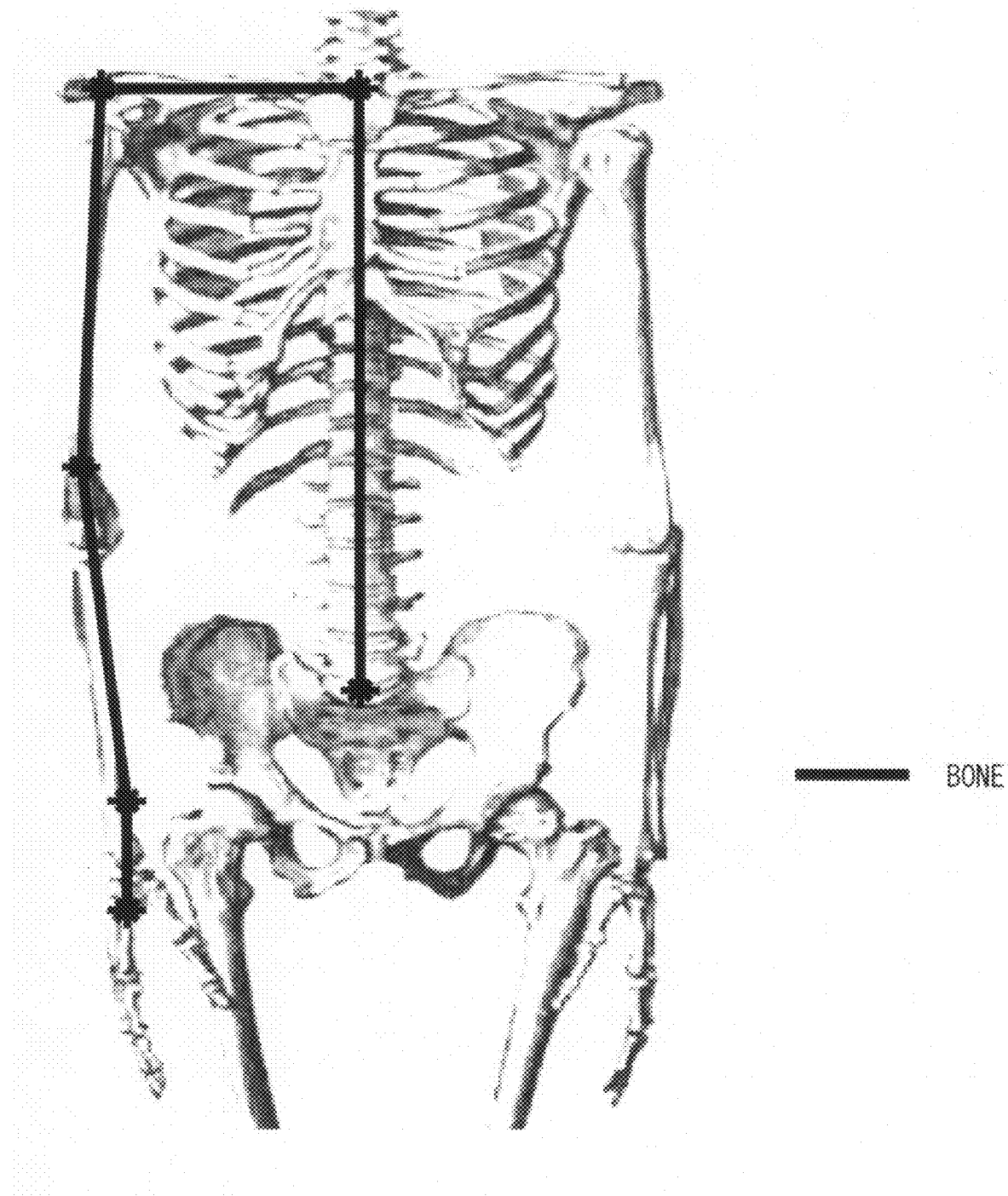
FIG. 6 relates to an example of the present invention and is a drawing illustrating a visualized skeleton model.

FIG. 6 is a rigid link model of bones of a living body. In the rigid link model, the right part of the upper body of a human was simplified to have 5 links and 13 degrees of freedom with joints existing in the hip, the neck, the shoulder, the elbow, and the wrist. Data of the link model includes information of the length of each link, the mass of each link, and the moment of inertia of each link. Specific values of each information were set by referring to a published database (MotCo project: http://www.motco.dir.bg/). More specifically, by searching the database with use of heights and weights, data of the length of each link, the mass of each link, and the moment of inertia of each link were obtained, and these data were assigned as the above information. The position of the center of the mass was set to the midpoint of each link.

Figure 7:
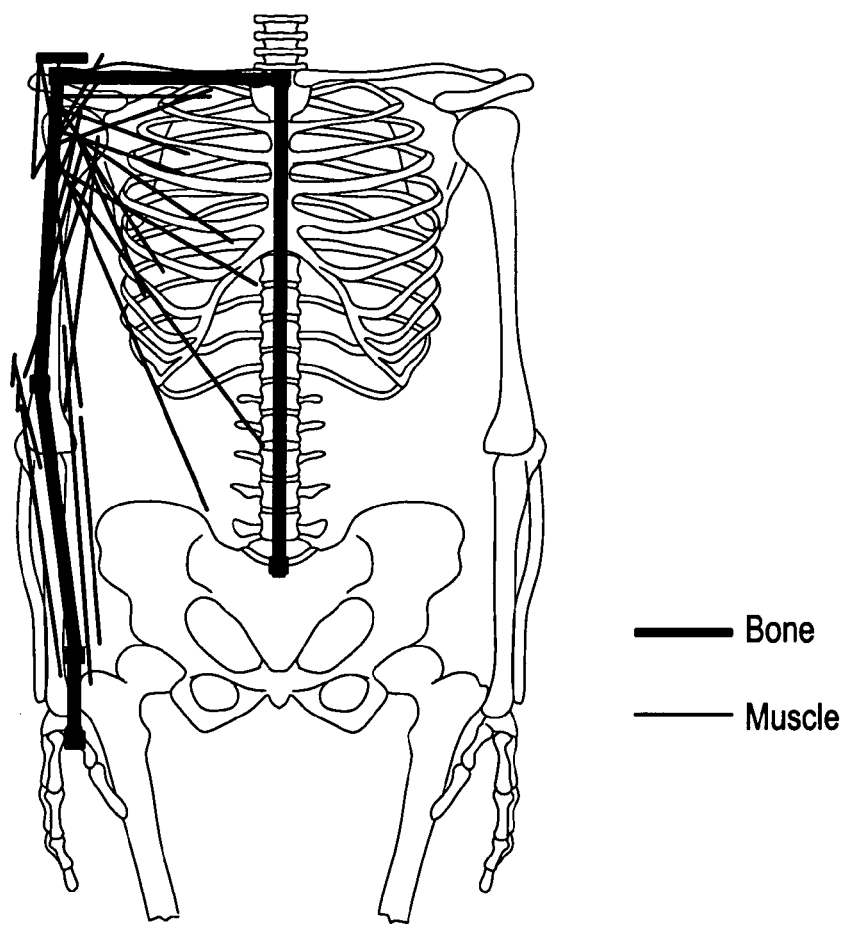
FIG. 7 relates to the example of the present invention and is a drawing illustrating a visualized musculoskeletal model.

FIG. 7 shows a model obtained by applying human muscles to the skeletal model. As illustrated in FIG. 7, muscles in the musculoskeletal model were provided in such a manner that attachment points (start points and end points) of 41 muscles that are across an elbow or a wrist and via-points where muscles touch parts of bones were provided according to anatomical knowledge. The provided muscles were pectoralis major muscles 1 and 2, latissimus dorsi muscles 1, 2, and 3, subscapularis muscle, deltoid muscle (anterior head), deltoid muscle (external head), deltoid muscle (posterior head), supraspinatus muscle, infraspinatus muscle, teres major muscle, teres minor muscle, coracobrachialis muscle, biceps brachii muscle (long head and short head), brachialis muscle, brachioradialis muscle, triceps brachii muscle (long head, internal head, and external head), anconeus muscle, flexor carpi ulnaris muscle, flexor carpi radialis muscle, palmaris longus muscle, flexor digitorum superficialis muscles 1 and 2, flexor digitorum profundus muscle, flexor pollicis longus muscle, pronator quadratus muscle, abductor pollicis longus muscle, pronator retes muscle, extensor carpi ulnaris muscle, extensor carpi radialis longus muscle, extensor carpi radialis brevis muscle, and extensor digitorum muscle. Each muscle was modeled as a weightless wire that passed through portions (start point, end point, and via-point) attached to bones. The muscle model data included information of the length of each muscle and information of the position where the muscle attached to bones. Numerical values obtained from the database were assigned to these parameters. The muscle model data and the skeletal model data were used to calculate moment arm of a muscle based on a joint angle.

Figure 8:
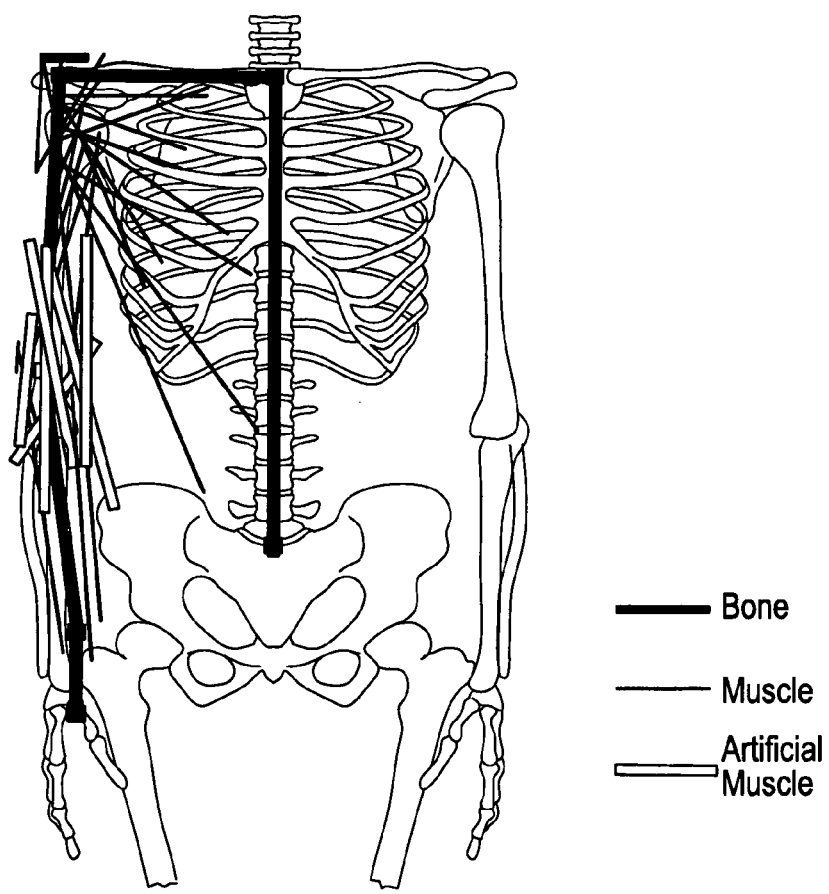
FIG. 8 relates to the example of the present invention and is a drawing illustrating a visualized muscle/artificial muscle integrated model.
Figure 9:
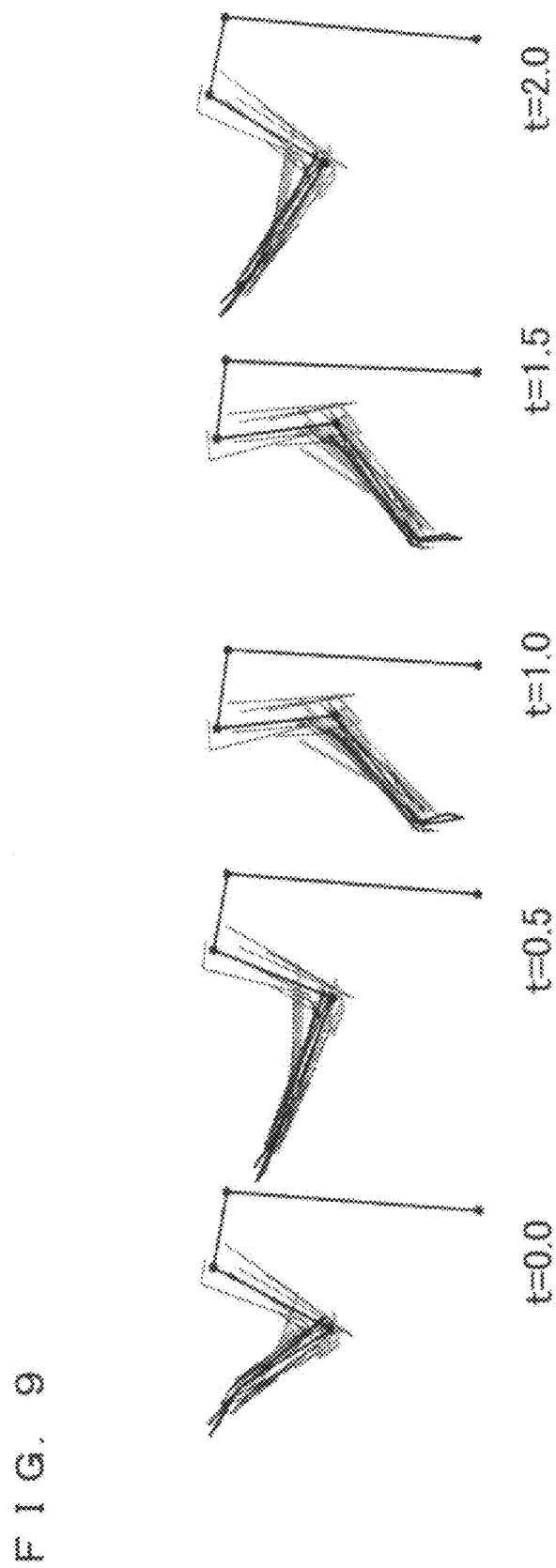
FIG. 9 relates to the example of the present invention and is a drawing illustrating visualized information obtained from an extension and flexion motion of an elbow.

FIG. 8 illustrates a muscle/artificial muscle integrated model in which the musculoskeletal model of a living body is combined with artificial muscles of the power assisting device. As illustrated in FIG. 8, 6 artificial muscles (AFMs 1 to 6) that assisted flexion and extension of an elbow were used. As with the muscle, the model of each artificial muscle was modeled as a weightless wire that passed through portions (start point, end point, and via-point) attached to bones. The artificial muscle model data included information of the length of each artificial muscle and information of the position where the artificial muscle attached to bones. The artificial muscle model data was combined with the skeletal model data to calculate moment arm of an artificial muscle based on a joint angle.

(Motion Information Acquiring Process and Motion Information Acquiring Means)

A driving force of an artificial muscle in the present example was designed in such a manner that a load to be applied on a specific muscle in an extension and flexion motion of an elbow (without pronation and supination) was changed. In this motion, the elbow was extended and flexed without rotations of the forearm and the wrist. The extension and flexion motion of the elbow was repeated for four times in the present example.

Then, using VICON (VICON 512 manufactured by Vicon Motion Systems) as a motion information acquiring section, the extension and flexion motion of the elbow was measured at 120 Hz of a sampling frequency. The motion information thus obtained is visualized in FIG. 9.

(Joint Torque Calculating Process and Joint Torque Calculating Means)

The angle of each joint, the angular velocity of each joint, and the angular acceleration of each joint were specified based on the motion information obtained from the above measurement, and are subjected to calculation of inverse dynamics. Thus, joint torque for each joint was calculated. The joint torque was calculated with respect to each instant. Then, a table indicative of relation between time and the joint torque (joint torque table) was stored in the storage section. FIG. 10 is a graph indicative of the joint torque table.

(Muscle Force Calculating Process and Muscle Force Calculating Means)

It was assumed that joint i (i is an integer from 1 to 5) was each joint, j muscles were across joint i, $r_j$ was a distance from the joint axis of joint i to the attachment point and the via-point of muscle j that was across joint i, and $f_j$ was a muscle force of muscle j. At that time, torque $\tau_i$ of joint i is represented by an equation as presented below.

$$\tau_i = \sum_j r_j \times f_j \tag{1}$$

Further, the possible range of muscle $f_j$ of each muscle was represented by an inequality:

$$0 \leq f_j \leq kA_j \tag{2}$$

where $k=0.7\times10^6$[N/m$^2$], $A_j$ is the physiological cross-sectional area of muscle j, and the value of $A_j$ was that described in Documents 4 to 6 as cited below.

Under the constraint condition of Equation (1) regarding joint torque and Inequality (2) regarding the possible range of a muscle force, muscle force $f_j$ of each muscle was calculated so that performance function u(f) as presented below has the minimum value.

$$u(f) = \sum_{j=1}^{41} \left(\frac{f_j}{A_j}\right)^2 \quad (3)$$

Figure 11:
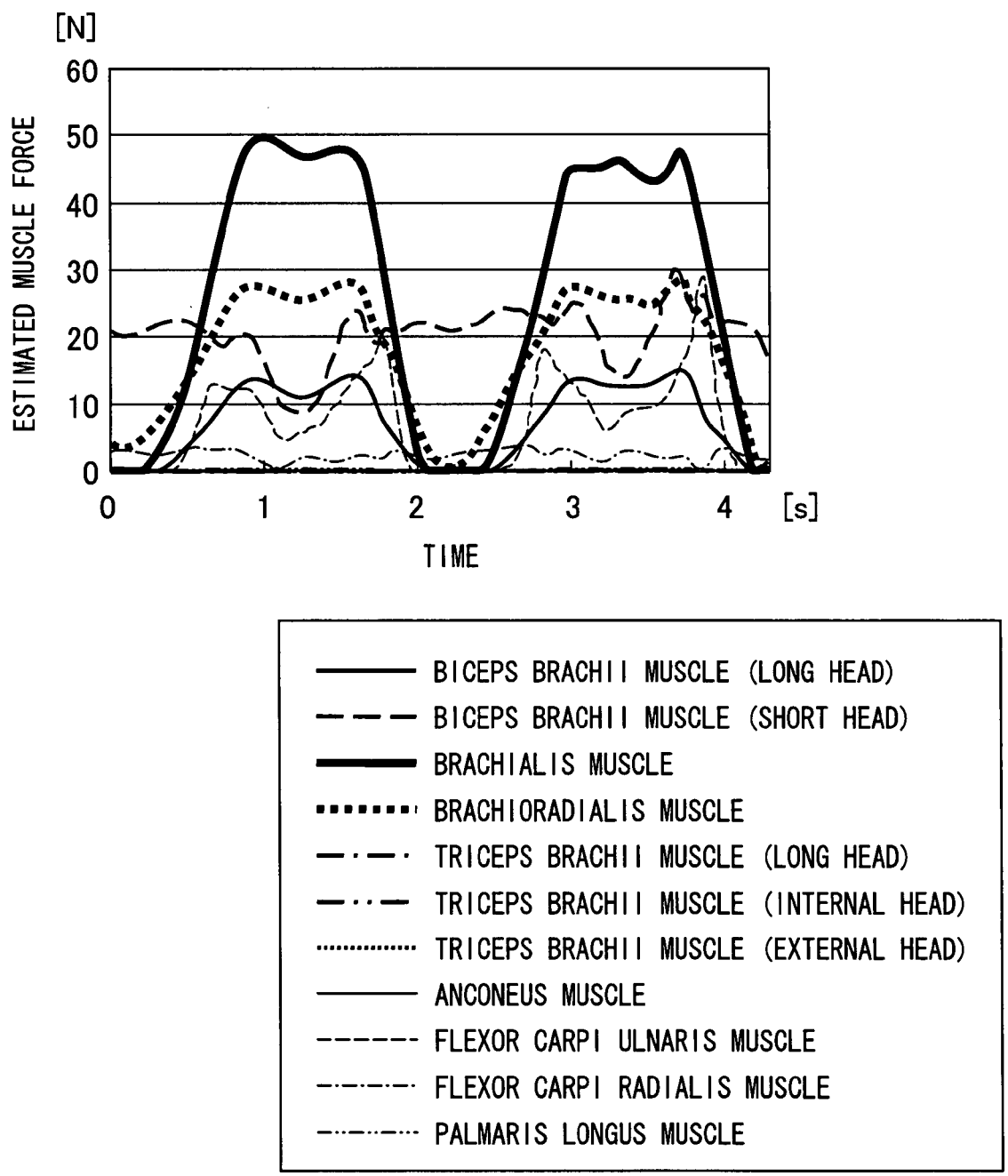
FIG. 11 relates to the example of the present invention and is a graph illustrating an estimated muscle force table.

For calculating the minimum value of u(f), quadprog function included in Optimization Toolbox of MATLAB® was used. $f_j$ was calculated with respect to each instant and a table indicative of relation between time and the calculated muscle force (estimated muscle force) was stored in the storage section. FIG. 11 is a graph indicative of estimated muscle force tables for 11 muscles that are necessary for the extension and flexion motion.

[Document 4]
J. Biggs et al.: "A three-dimensional kinematic model of the human long finger and the muscles that actuate it", Medical Engineering & Physics, 21(9), pp. 625-639, 1999.
[Document 5]
MotCo project: http://www.motco.dir.bg/Data/PCSA.html
[Document 6]
H. E. J. Veeger et al.: "Inertia and muscle contraction parameters for musculoskeletal modelling of the shoulder mechanism", J. Biomechanics, 24, 7, pp. 615-629, 1991.

(Muscle Force Assigning Process and Muscle Force Input Section)

Figure 12:
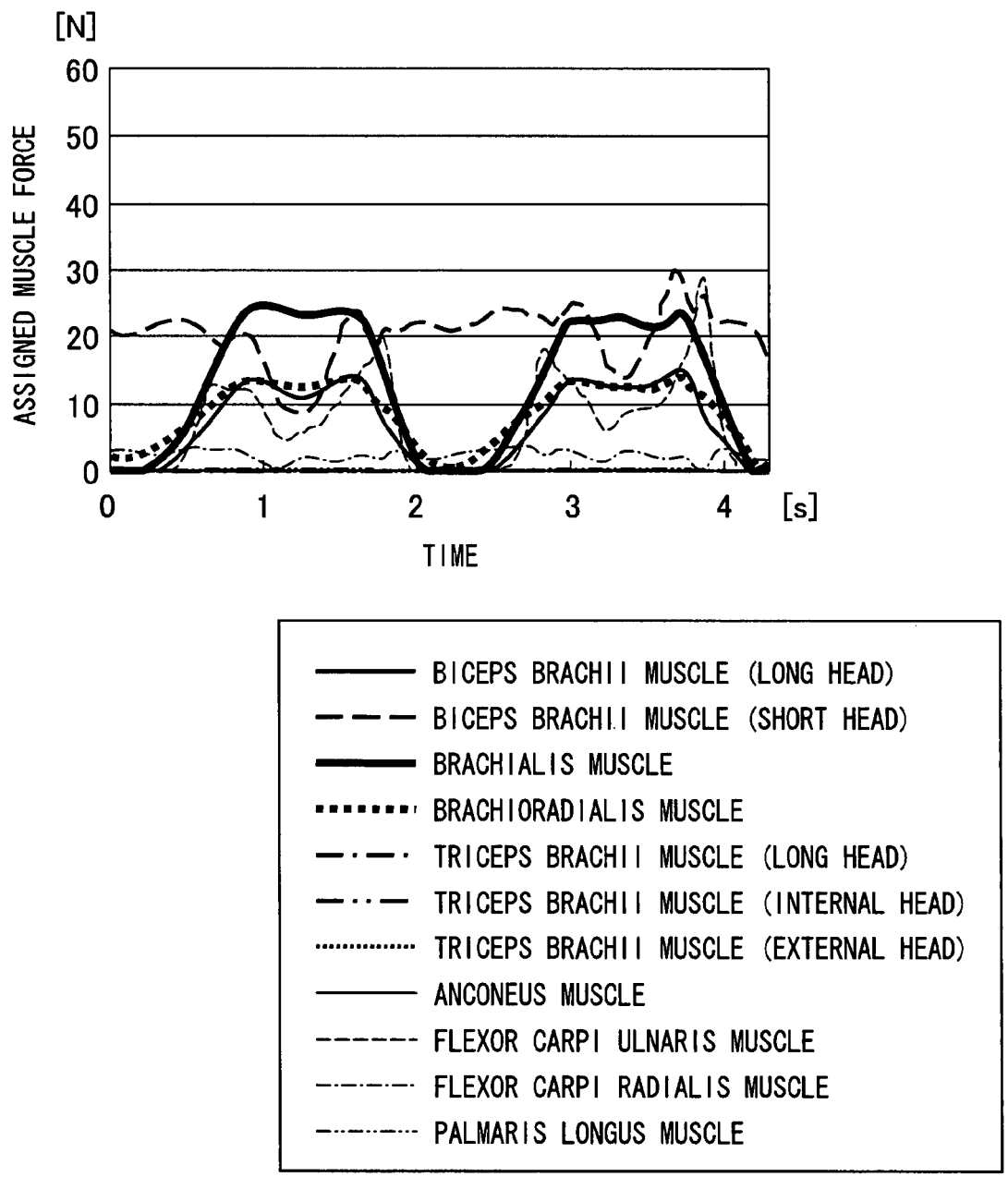
FIG. 12 relates to the example of the present invention and is a graph illustrating an assigned muscle force table.

In the present example, muscle forces of the 41 muscles were assigned so that muscle forces of brachialis muscle and brachioradialis muscle were half (0.5 times) of the muscle forces calculated in the muscle force calculating process (estimated muscle forces), and muscle forces of other muscles were the same as the muscle forces calculated in the muscle force calculating process. That is, in accordance with the muscle forces calculated in the muscle force calculating process, only the muscle forces of brachialis muscle and brachioradialis muscle were calculated so as to be half (0.5 times), and the calculated muscle forces were regarded as assigned muscle forces of brachialis muscle and brachioradialis muscle. As for other muscles, estimated muscle forces of the other muscles were regarded as assigned muscle forces. Then, a table indicative of relation between time and the assigned muscles (assigned muscle table) was stored in the storage section. FIG. 12 is a graph indicative of assigned muscle force tables. The graph indicates assigned muscle force tables of main muscles that generate muscle forces in the extension and flexion of the elbow, and muscle forces of other muscles were always 0.

(Driving Force Calculating Process and Driving Force Calculating Means)

Subsequently, muscle forces of artificial muscles in the muscle/artificial muscle integrated model having the 41 muscles and the 6 artificial muscles were calculated under the constraint condition of the joint torque obtained in the joint torque calculating process and the muscle forces assigned in the muscle force assigning process.

That is, when it was assumed that joint i (i is an integer from 1 to 5) was each joint, j number of muscles and artificial muscles were across joint i, $r_j$ was a distance from the joint axis of joint i to the attachment point and the via-point of muscle j or artificial muscle j that was across joint i, and $f_j$ was a muscle force of muscle j or artificial muscle j. At that time, torque $\tau_i$ of joint i is represented by Equation (1). Under the constraint conditions of Equation (1), the muscle forces $f_j$ that have been assigned in the muscle force assigning process, and Inequality (2), driving forces $f_j$ of artificial muscles were calculated so that performance function u(f) as presented below has the minimum value $$u(f) = \sum_{j=1}^{6} \left(\frac{f_j}{A_j}\right)^2 \quad (4)$$

where $f_j$ was the driving force of the artificial muscle j and $A_j$ was the cross-sectional area of the artificial muscle.

$f_j$ was calculated with respect to each instant and tables indicative of relations between time and the calculated driving forces of the artificial muscles (driving force tables) were stored in the storage section. FIG. 13 is a graph indicative of the driving force tables.

The artificial muscles of the present example were supposed to be bundles of the same actuators. Therefore, the maximum driving force of each artificial muscle was in proportion to the number of the actuators. Further, in a case where each artificial muscle generated the same driving force, the load applied on each artificial muscle was in inverse proportion to the number of the actuators (cross-sectional areas of the driving sections). In the present example, the driving force of each artificial muscle was optimized with use of Equation (4) as presented above. That is, with Equation (4), the driving force of each artificial muscle was optimized so that the sum of a square of {(the driving force of an artificial muscle)/(the cross-sectional area of the artificial muscle)} had the minimum value. Accordingly, with Equation (4), the driving force per one actuator included in each artificial muscle was optimized to be as equal as possible to one another and as small as possible. Consequently, it was possible to reduce the load applied on each actuator.

(Muscle Force Recalculating Process and Muscle Force Recalculating Means)

Subsequently, the muscle force of each muscle of the living body in the muscle/artificial muscle integrated model was recalculated under the constraint conditions of the joint torque calculated in the joint torque calculating process and the driving force of each artificial muscle calculated in the driving force calculating process.

Specifically, muscle force $f_j$ of each muscle of the living body was calculated so that performance function u(f) of Equation (3) had the minimum value under the constraint conditions of Equation (1), driving force $f_j$ of each artificial muscle calculated in the driving force calculating process, and Inequality (2).

Figure 14:
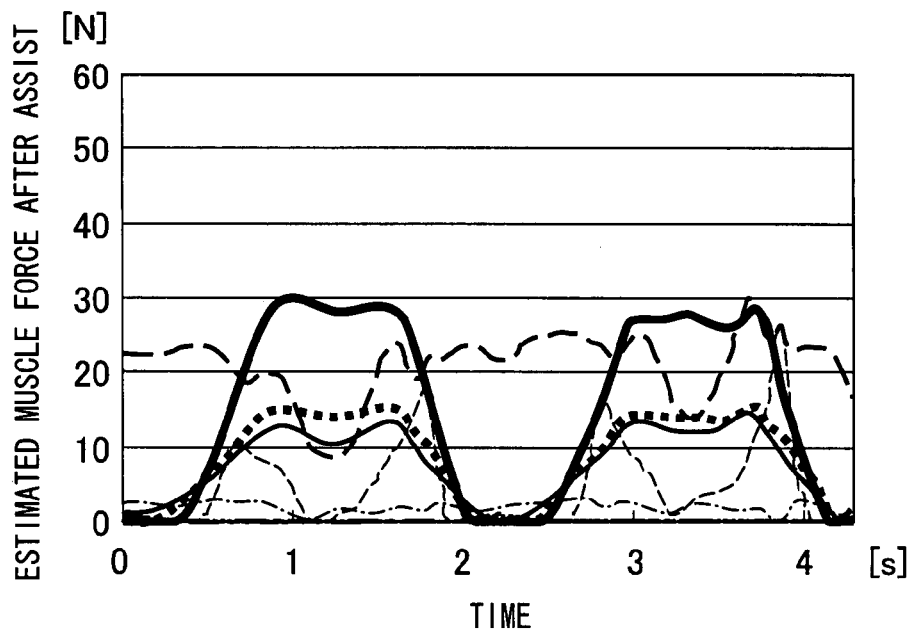
FIG. 14 relates to the example of the present invention and is a graph illustrating an estimated muscle-force-after-assist table.

Then, tables indicative of relations between time and the calculated muscle forces (estimated muscle-force-after-assist tables) were stored in the storage section. FIG. 14 is a graph indicative of the estimated-muscle-force-after-assist tables.

(Comparison Process and Comparison Means)

The muscle force of each muscle that had been assigned in the muscle force assigning process was compared with the muscle force of each muscle calculated in the muscle force recalculating process, and the result of the comparison was evaluated. Specifically, the assigned muscle force table was compared with the muscle-force-after-assist table so as to check a difference between the assigned muscle force table and the muscle-force-after-assist table. Comparison between FIG. 12 and FIG. 14 showed that the muscle force after assist was substantially the same as the assigned muscle force. That is, comparison between muscle forces after assist and muscle forces before assist showed that muscle forces of brachialis muscle and brachioradialis muscle after assist got approximately half of those before assist while muscle forces of other muscles after assist were substantially the same as those before assist. This showed that the driving force calculating method and the driving force calculating device of the present example functioned well.

[Supplement]

As described above, the driving force calculating device of the present invention includes: a muscle force input section to which an assigned muscle force to be generated in assisting and/or resisting a rotational motion is input; and driving force calculating means for calculating the driving force of the driving section based on the assigned muscle force and on joint torque necessary for the rotational motion, so that the assigned muscle force and the driving force of the driving section generate the joint torque necessary for the rotational motion.

Therefore, as described above, it is possible to calculate a driving force so that a predetermined load is applied on a muscle when the power assisting device assists or resists a predetermined motion.

It is preferable to arrange the driving force calculating device of the present invention so that the driving force calculating means calculates the driving force of the driving section using three-dimensional structural information including at least information indicative of positions of (i) the bones and the muscle of the living body and (ii) the driving section of the power assisting device, and the joint torque is represented by an equation:

$$\tau_i = \sum_j r_j \times f_j$$

where i is a numeral order of a joint, $\tau_i$ is joint torque at joint i, j is a numeral order of a muscle or a driving section that is across joint i, $r_j$ is moment arm of muscle j or driving section j, and $f_j$ is a muscle force of muscle j or a driving force of driving section j.

Joint torque $\tau_i$ is joint torque necessary for the rotational motion. Moment arm $r_j$ of muscle j and driving section j can be obtained from the three-dimensional structural information. Therefore, the relational expression of $f_j$ can be obtained from the equation.

Further, the driving force calculating device of the present invention may be arranged so that, under constraint conditions of the assigned muscle force and the joint torque necessary for the rotational motion, the driving force calculating means calculates the driving force of the driving section by calculating $f_j$ so that performance function u(f) has a minimum value, the performance function u(f) being represented by an equation:

$$u(f) = \sum_{j=1}^{n} \left(\frac{f_j}{A_j}\right)^m$$

where n is a sum of (i) the number of a muscle for which an assigned muscle force has not been input to the muscle force input section and (ii) the number of the driving section, j is a numeral order of the muscle for which an assigned muscle force has not been input to the muscle force input section or j is a numeral order of the driving section, $f_j$ is a muscle force of a muscle in j-th order or a driving force of a driving section in j-th order, $A_j$ is a physiological cross-sectional area of a muscle in a case where j is a muscle and $A_j$ is a value based on a maximum driving force in a case where j is a driving section, and m is any integer of 2 or more.

There are a plurality of muscles whose muscle forces are to be obtained, and therefore it is impossible to directly obtain a fixed solution for individual muscle forces (i.e. $f_j$) based on the joint torque. However, by optimizing $f_j$ using the performance function u(f), it is possible to determine values of the muscle forces of respective muscles and the driving forces of respective driving sections.

Further, it is preferable to arrange the driving force calculating device of the present invention so as to further include muscle force calculating means for calculating a muscle force necessary for the rotational motion in a case where the power assisting device neither assists nor resists the rotational motion, the muscle force being calculated based on the joint torque necessary for the rotational motion, the assigned muscle force being input to the muscle force input section based on the muscle force calculated by the muscle force calculating means.

With the arrangement, the muscle force calculating means can calculate a muscle force necessary for each muscle at a time when a user performs the rotational motion without wearing the power assisting device. The assigned muscle force is input to the muscle force input section based on the calculated muscle force. Therefore, the user can assign a muscle force by assigning, for example, a ratio etc. to the muscle force at the time when the user does not wear the power assisting device.

Further, it is preferable to arrange the driving force calculating device of the present invention so as to further include: muscle force recalculating means for calculating a muscle force necessary for the rotational motion in a case where the power assisting device assists and/or resists the rotational motion, the muscle force being calculated based on (i) the driving force calculated by the driving force calculating means and (ii) the joint torque necessary for the rotational motion; and comparison means for comparing the muscle force calculated by the muscle force recalculating means with the assigned muscle force having been input to the muscle force input section.

With the arrangement, it is possible to compare (i) the muscle force of each muscle at a time when the power assisting device assists and/or resists the rotational motion by using the driving force calculated by the driving force calculating means with (ii) the assigned muscle force, and to check whether the two muscle forces are the same with each other or not. Consequently, it is possible to avoid unexpected malfunction.

Further, it is preferable to arrange the driving force calculating device of the present invention so as to further include joint torque calculating means for calculating the joint torque necessary for the rotational motion, the joint torque calculated by the joint torque calculating means being used in calculation of the driving force or the muscle force by at least one of the driving force calculating means, the muscle force calculating means, and the muscle force recalculating means.

With the arrangement, the power assisting device can calculate each joint torque based on motion information regarding the rotational motion. Consequently, it is unnecessary to calculate the joint torque with use of other means. This enables the user to easily use the power assisting device.

Further, it is preferable to arrange the driving force calculating device of the present invention so as to further include motion information acquiring means for acquiring motion information regarding the rotational motion, the joint torque calculating means calculating the joint torque necessary for the rotational motion based on the motion information acquired by the motion information acquiring means.

With the arrangement, the power assisting device calculates joint torque necessary for a rotational motion merely by the user actually performing the rotational motion. Consequently, the user can more easily set the rotational motion.

Each means of the driving force calculating device may be realized by hardware or may be realized by computer executing a program. Specifically, the program of the present invention is a program for causing a computer to function as each means of the driving force calculating device. Further, the storage medium of the present invention is a storage medium in which the program is stored.

When the program is executed by a computer, the computer functions as each means of the driving force calculating device. Consequently, it is possible to realize driving force calculating means capable of regulating a load applied on a muscle when the user performs the rotational motion of a joint.

Further, the driving force calculating method of the present invention includes the steps of: (a) assigning a desired muscle force to the muscle; and (b) calculating the driving force of the driving section based on the muscle force assigned in the step (a) and joint torque necessary for the rotational motion, so that the muscle force assigned in the step (a) and the driving force of the driving section generate the joint torque necessary for the rotational motion.

Therefore, as described above, it is possible to calculate a driving force so that a desired load is applied on a muscle when the power assisting device assists or resists a predetermined motion.

Further, it is preferable to arrange the driving force calculating method of the present invention so that, in the step (b), the driving force of the driving section is calculated using three-dimensional structural information including at least information indicative of positions of (i) the bones and the muscle of the living body and (ii) the driving section of the power assisting device, and the joint torque is represented by an equation:

$$\tau_i = \sum_j r_j \times f_j$$

where i is a numeral order of a joint, $\tau_i$ is joint torque at joint i, j is a numeral order of a muscle or a driving section that is across joint i, $r_j$ is moment arm of muscle j or driving section j, and $f_j$ is a muscle force of muscle j or a driving force of driving section j.

Joint torque $\tau_i$ is joint torque necessary for the rotational motion. Moment arm $r_j$ of muscle j and driving section j can be obtained from the three-dimensional structural information. Therefore, the relational expression of $f_j$ can be obtained from the equation.

Further, the driving force calculating method of the present invention may be arranged so that, under constraint conditions of the muscle force assigned in the step (a) and the joint torque necessary for the rotational motion, the driving force of the driving section in a case where the power assisting device assists and/or resists the rotational motion is calculated by calculating $f_j$ so that performance function u(f) has a minimum value, the performance function u(f) being represented by an equation:

$$u(f) = \sum_{j=1}^{n} \left(\frac{f_j}{A_j}\right)^m$$

where n is a sum of (i) the number of a muscle for which a muscle force has not been assigned in the step (a) and (ii) the number of the driving section, j is a numeral order of the muscle for which a muscle force has not been assigned in the step (a) or j is a numeral order of the driving section, $f_j$ is a muscle force of a muscle in j-th order or a driving force of a driving section in j-th order, $A_j$ is a physiological cross-sectional area of a muscle in a case where j is a muscle and $A_j$ is a value based on a maximum driving force in a case where j is a driving section, and m is any integer of 2 or more.

Further, it is preferable to arrange the driving force calculating method of the present invention so as to further include the step of (c) calculating a muscle force necessary for the rotational motion in a case where the power assisting device neither assists nor resists the rotational motion, the muscle force being calculated based on the joint torque necessary for the rotational motion, in the step (a), a desired muscle force being assigned to a muscle based on the muscle force calculated in the step (c).

With the arrangement, it is possible to calculate a muscle force necessary for each muscle at a time when the user performs a rotational motion without wearing the power assisting device. The user can input the assigned muscle force based on the calculated muscle force. Therefore, by setting, for example, a ratio etc. to a state where the user does not wear the power assisting device, it is possible to assign a muscle force. Therefore, it is possible to more easily assign a muscle force.

Further, it is preferable to arrange the driving force calculating method of the present invention so as to further include the step of: (d) calculating a muscle force of a muscle necessary for the rotational motion in a case where the power assisting device assists and/or resists the rotational motion, the muscle force being calculated based on (i) the driving force calculated in the step (b) and (ii) the joint torque necessary for the rotational motion; and (e) comparing the muscle force calculated in the step (d) with the muscle force assigned in the step (a).

With the arrangement, it is possible to compare (i) the muscle force of each muscle at a time when the power assisting device assists and/or resists the rotational motion by using the driving force calculated in the step (b) with (ii) the assigned muscle force, and to check whether the two muscle forces are the same with each other or not. Consequently, it is possible to avoid unexpected malfunction.

Further, it is preferable to arrange the driving force calculating method of the present invention so as to further include the step of (f) calculating the joint torque necessary for the rotational motion, the joint torque calculated in the step (f) being used in calculation of the driving force or the muscle force in at least one of the steps (b), (c), and (d).

With the arrangement, it is possible to calculate each joint torque based on motion information regarding the rotational motion.

Further, the power assisting device of the present invention includes a storage section in which data of the driving force calculated by the driving force calculating device or through the driving force calculating method is stored.

Therefore, it is possible to regulate a load applied on a muscle when the user performs a predetermined motion.

Further, it is preferable to arrange the power assisting device of the present invention so as to further include an input section, a plurality of data of a driving force being stored in the storage section in such a manner that the data is associated with information of the rotational motion which information has been used in calculating the driving force, information of the rotational motion being input to the input section, and based on the information of the rotational motion input to the input section, the driving force control section retrieving, from the storage section, corresponding data of the driving force, and the driving force control section controlling the driving section based on the retrieved data.

With the arrangement, when the information of the rotational motion is input to the input section, the driving force control section retrieves data of a driving force which is associated with the input information of the rotational motion, and controls the control section based on the retrieved data of a driving force. Therefore, the power assisting device can assist a desired rotational motion out of a plurality of rotational motions that are provided beforehand.

Further, it is preferable to arrange the power assisting device of the present invention so that a plurality of data of a driving force are stored in the storage section in such a manner that the data is associated with information of a muscle force assigned in the step (a) (assigned muscle force), information of a muscle force assigned to a muscle is input to the input section, and based on the information of a muscle force input to the input section, the driving force control section retrieves, from the storage section, corresponding data of the driving force, and the driving force control section controlling the driving section based on the retrieved data.

With the arrangement, when the information of the assigned muscle force is input to the input section, the driving force control section retrieves data of a driving force which is associated with the input information of the muscle force, and controls the control section based on the retrieved data of a driving force. Therefore, the power assisting device can assist the rotational motion so that a desired assigned muscle force is selected out of a plurality of assigned muscle forces that are provided beforehand.

Further, the computer-readable storage medium of the present invention is a computer-readable storage medium, which is used as a storage section of the power assisting device, and in which the data of a driving force is stored. The driving force control section controls based on the data stored in the storage medium. Therefore, it is possible to realize a power assisting device capable of assisting a rotational motion while regulating a load applied on a muscle when the user performs a rotational motion of a joint.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

Further, numerical ranges that are not disclosed in the present specification and that are in accordance with the spirit of the present invention are also included in the present invention.

INDUSTRIAL APPLICABILITY

Application of the present invention to a power assisting device allows application of a desired load on a muscle in a particular region. Thus, effective muscle training and effective rehabilitation can be achieved. Further, a user can perform some rehabilitation exercises at home. In this manner, the present invention is highly applicable to the field of sports and medical services.

The invention claimed is:

1. A driving force calculating device for calculating a driving force of a driving section of a power assisting device that is worn by a living body having bones with a joint and a muscle and that assists and/or resists a rotational motion of the joint with use of the driving section fixed to the bones across the joint, the driving force calculating device comprising:
a muscle force input section to which an assigned muscle force that is to be generated in assisting and/or resisting the rotational motion is input; and
a driving force calculating section for calculating the driving force of the driving section based on the assigned muscle force and on joint torque necessary for the rotational motion, so that the assigned muscle force and the driving force of the driving section generate the joint torque necessary for the rotational motion,
wherein, under constraint conditions of the assigned muscle force and the joint torque necessary for the rotational motion, the driving force calculating section calculates the driving force of the driving section by calculating $f_j$ so that performance function $u(f)$ has a minimum value, the performance function $u(f)$ being represented by an equation:

$$u(f) = \sum_{j=1}^{n} \left(\frac{f_j}{A_j}\right)^m$$

where n is a sum of (i) the number of a muscle for which an assigned muscle force has not been input to the muscle force input section and (ii) the number of the driving section, j is a numeral order of the muscle for which an assigned muscle force has not been input to the muscle force input section or j is a numeral order of the driving section, $f_j$ is a muscle force of a muscle in j-th order or a driving force of a driving section in j-th order, $A_j$ is a physiological cross-sectional area of a muscle in a case where j is a muscle and $A_j$ is a value based on a maximum driving force in a case where j is a driving section, and m and n are any integer of 2 or more.

2. The driving force calculating device as set forth in claim 1, wherein the driving force calculating section calculates the driving force of the driving section based on the assigned muscle force and on the joint torque necessary for the rotational motion, the driving force being calculated using three-dimensional structural information including at least information indicative of positions of (i) the bones and the muscle of the living body and (ii) the driving section of the power assisting device.

3. The driving force calculating device as set forth in claim 1, wherein
the driving force calculating section calculates the driving force of the driving section by using three-dimensional structural information including at least information indicative of positions of (i) the bones and the muscle of the living body and (ii) the driving section of the power assisting device, and the joint torque is represented by an equation:

$$\tau_i = \sum_j r_j \times f_j$$

where i is a numeral order of a joint, $\tau_i$ is joint torque at joint i, j is a numeral order of a muscle or a driving section that is across joint i, $r_j$ is moment arm of muscle j or driving section j, and $f_j$ is a muscle force of muscle j or a driving force of driving section j.

4. The driving force calculating device as set forth in claim 3, wherein the driving force calculating section calculates $f_j$ as a muscle force necessary for the rotational motion in a case where the power assisting device neither assists nor resists the rotational motion, and the driving force calculating section multiplies the muscle force thus calculated by a desired ratio to obtain the assigned muscle force, the calculation of $f_j$ being carried out so that performance function u(f) has a minimum value, the performance function u(f) being represented by an equation:

$$u(f) = \sum_{j=1}^{n} \left(\frac{f_j}{A_j}\right)^m$$

where n is a number of a muscle, $A_j$ is a physiological cross-sectional area of a muscle, and m is any integer of 2 or more.

5. The driving force calculating device as set forth in claim 1, further comprising a muscle force calculating section for calculating a muscle force necessary for the rotational motion in a case where the power assisting device neither assists nor resists the rotational motion, the muscle force being calculated based on the joint torque necessary for the rotational motion, the assigned muscle force being input to the muscle force input section based on the muscle force calculated by the muscle force calculating section.

6. The driving force calculating device as set forth in claim 1, further comprising:

a muscle force recalculating section for calculating a muscle force necessary for the rotational motion in a case where the power assisting device assists and/or resists the rotational motion, the muscle force being calculated based on (i) the driving force calculated by the driving force calculating section and (ii) the joint torque necessary for the rotational motion; and a comparison section for comparing the muscle force calculated by the muscle force recalculating section with the assigned muscle force having been input to the muscle force input section.

7. The driving force calculating device as set forth in claim 1, further comprising a joint torque calculating section for calculating the joint torque necessary for the rotational motion, the joint torque calculated by the joint torque calculating section being used in calculation of the driving force or the muscle force by the driving force calculating section.

8. The driving force calculating device as set forth in claim 7, further comprising a motion information acquiring section for acquiring motion information regarding the rotational motion, the joint torque calculating section calculating the joint torque necessary for the rotational motion based on the motion information acquired by the motion information acquiring section.

9. A non-transitory program, causing a computer to function as the driving force calculating device set forth in claim 1.

* * * * *